(12) United States Patent
Wallace et al.

(10) Patent No.: US 10,751,140 B2
(45) Date of Patent: Aug. 25, 2020

(54) ROBOTIC MEDICAL SYSTEMS WITH HIGH FORCE INSTRUMENTS

(71) Applicant: Auris Health, Inc., Redwood City, CA (US)

(72) Inventors: Daniel T. Wallace, Santa Cruz, CA (US); Travis Michael Schuh, Los Altos, CA (US); Spencer James Witte, Los Altos, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/429,441

(22) Filed: Jun. 3, 2019

(65) Prior Publication Data

US 2019/0374297 A1 Dec. 12, 2019

Related U.S. Application Data

(60) Provisional application No. 62/682,049, filed on Jun. 7, 2018.

(51) Int. Cl.
*A61B 34/00* (2016.01)
*A61B 17/29* (2006.01)
*A61B 34/30* (2016.01)

(52) U.S. Cl.
CPC .............. *A61B 34/71* (2016.02); *A61B 17/29* (2013.01); *A61B 2017/2936* (2013.01); *A61B 2017/2947* (2013.01); *A61B 2034/301* (2016.02); *A61B 2034/302* (2016.02); *A61B 2034/303* (2016.02)

(58) Field of Classification Search
CPC ............ A61B 17/29; A61B 2017/2936; A61B 2017/2947; A61B 34/71; A61B 2034/301; A61B 2034/302; A61B 2034/303
See application file for complete search history.

(56) References Cited

U.S. PATENT DOCUMENTS

| | | |
|---|---|---|
| 3,763,860 A | 10/1973 | Clarke |
| 4,040,413 A | 8/1977 | Ohshiro |
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |

(Continued)

FOREIGN PATENT DOCUMENTS

| | | |
|---|---|---|
| EP | 1 321 106 | 6/2003 |
| EP | 1 849 423 | 10/2007 |

(Continued)

*Primary Examiner* — Ashley L Fishback
(74) *Attorney, Agent, or Firm* — Knobbe Martens Olson & Bear LLP

(57) ABSTRACT

A robotic system can include a high force instrument that amplifies input forces such that output forces are greater than input forces. The high force instrument can include an end effector. The high force instrument can further include a first pulley configured to rotate about a pulley axis and a first jaw member connected to the first pulley by a first drive pin. The high force instrument can also include a second pulley configured to rotate about the pulley axis and a second jaw member connected to the second pulley by a second drive pink. A link can provide a first pivot point about which the first jaw member can pivot and a second pivot point about which the second jaw member can pivot.

20 Claims, 35 Drawing Sheets

(56) References Cited

U.S. PATENT DOCUMENTS

| | | |
|---|---|---|
| 4,747,405 A | 5/1988 | Leckrone |
| 4,854,301 A | 8/1989 | Nakajima |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,618,371 B2 | 11/2009 | Younge et al. |
| 7,736,356 B2 | 6/2010 | Cooper et al. |
| 7,850,642 B2 | 12/2010 | Moll et al. |
| 7,935,059 B2 | 5/2011 | Younge et al. |
| 7,963,288 B2 | 6/2011 | Rosenberg et al. |
| 7,963,911 B2 | 6/2011 | Turliuc |
| 7,972,298 B2 | 7/2011 | Wallace et al. |
| 7,974,681 B2 | 7/2011 | Wallace et al. |
| 7,976,539 B2 | 7/2011 | Hlavka et al. |
| 7,987,046 B1 | 7/2011 | Peterman |
| 8,002,713 B2 | 8/2011 | Heske |
| 8,005,537 B2 | 8/2011 | Hlavka et al. |
| 8,021,326 B2 | 9/2011 | Moll et al. |
| 8,038,598 B2 | 10/2011 | Khachi |
| 8,041,413 B2 | 10/2011 | Barbagli et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,172,747 B2 | 5/2012 | Wallace et al. |
| 8,187,173 B2 | 5/2012 | Miyoshi |
| 8,190,238 B2 | 5/2012 | Moll et al. |
| 8,257,303 B2 | 9/2012 | Moll et al. |
| 8,285,364 B2 | 10/2012 | Barbagli et al. |
| 8,311,626 B2 | 11/2012 | Hlavka et al. |
| 8,388,538 B2 | 3/2013 | Younge et al. |
| 8,388,556 B2 | 3/2013 | Wallace et al. |
| 8,394,054 B2 | 3/2013 | Wallace et al. |
| 8,409,136 B2 | 4/2013 | Wallace et al. |
| 8,409,172 B2 | 4/2013 | Moll et al. |
| 8,480,595 B2 | 7/2013 | Speeg |
| 8,498,691 B2 | 7/2013 | Moll et al. |
| 8,523,762 B2 | 9/2013 | Miyamoto et al. |
| 8,540,748 B2 | 9/2013 | Murphy et al. |
| 8,617,102 B2 | 12/2013 | Moll et al. |
| 8,801,661 B2 | 8/2014 | Moll et al. |
| 8,820,603 B2 | 9/2014 | Shelton et al. |
| 8,882,660 B2 | 11/2014 | Phee et al. |
| 8,926,603 B2 | 1/2015 | Hlavka et al. |
| 8,945,163 B2 | 2/2015 | Voegele et al. |
| 8,956,280 B2 | 2/2015 | Eversull et al. |
| 8,974,408 B2 | 3/2015 | Wallace et al. |
| 9,345,456 B2 | 5/2016 | Tsonton et al. |
| 9,358,076 B2 | 6/2016 | Moll et al. |
| 9,457,168 B2 | 10/2016 | Moll et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,629,682 B2 | 4/2017 | Wallace et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |

(56) References Cited

U.S. PATENT DOCUMENTS

| | | |
|---|---|---|
| 10,350,390 B2 | 7/2019 | Moll et al. |
| 10,482,599 B2 | 11/2019 | Mintz et al. |
| 10,524,866 B2 | 1/2020 | Srinivasan |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2006/0200026 A1 | 9/2006 | Wallace et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0027464 A1 | 1/2008 | Moll et al. |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0262480 A1 | 10/2008 | Stahler et al. |
| 2008/0262513 A1 | 10/2008 | Stahler et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0062602 A1 | 3/2009 | Rosenberg et al. |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0228020 A1 | 9/2009 | Wallace et al. |
| 2009/0248041 A1 | 10/2009 | Williams et al. |
| 2009/0248043 A1 | 10/2009 | Tierney et al. |
| 2009/0254083 A1 | 10/2009 | Wallace et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0257641 A1 | 10/2011 | Hastings et al. |
| 2011/0270273 A1 | 11/2011 | Moll et al. |
| 2011/0276085 A1 | 11/2011 | Krzyzanowski |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0116253 A1 | 5/2012 | Wallace et al. |
| 2012/0138586 A1 | 6/2012 | Webster et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296161 A1 | 11/2012 | Wallace et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1* | 6/2013 | Stefanchik .......... A61B 17/29 623/20.11 |
| 2013/0190741 A1 | 7/2013 | Moll et al. |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam |

(56) References Cited

U.S. PATENT DOCUMENTS

| | | |
|---|---|---|
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0080879 A1 | 3/2015 | Trees |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo et al. |
| 2015/0164596 A1 | 6/2015 | Romo |
| 2015/0201917 A1 | 7/2015 | Snow |
| 2015/0202085 A1 | 7/2015 | Lemonis |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0086929 A1 | 3/2017 | Moll et al. |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119481 A1 | 5/2017 | Romo et al. |
| 2017/0135706 A1 | 5/2017 | Frey |
| 2017/0151416 A1 | 6/2017 | Kutikov |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0215978 A1 | 8/2017 | Wallace et al. |
| 2017/0252096 A1 | 9/2017 | Felder |
| 2017/0265923 A1 | 9/2017 | Privitera |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0177556 A1 | 6/2018 | Noonan et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0239890 A1* | 8/2019 | Stokes ................. A61B 17/122 |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0101264 A1 | 4/2020 | Jiang |

FOREIGN PATENT DOCUMENTS

| | | |
|---|---|---|
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |

* cited by examiner

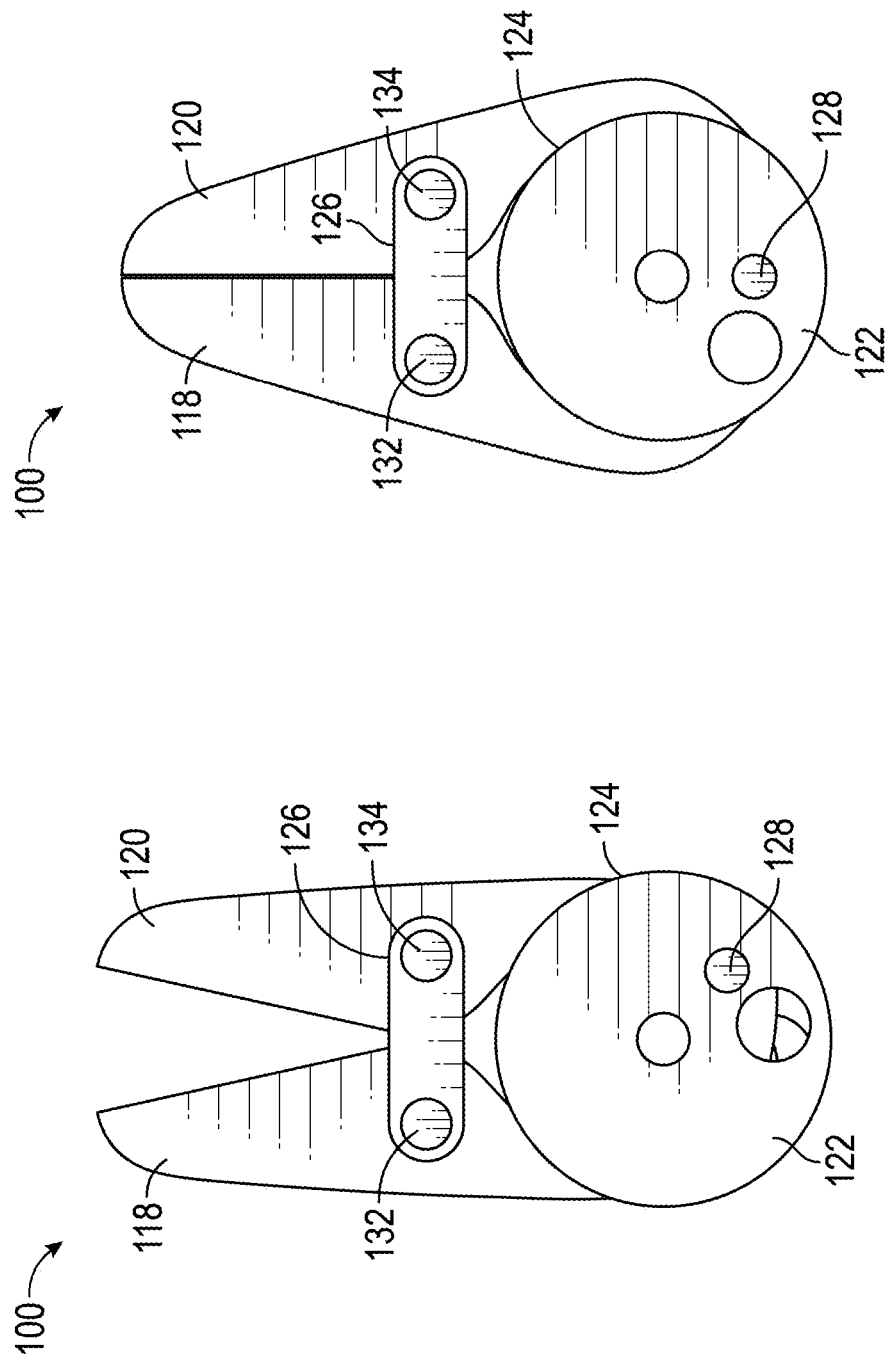

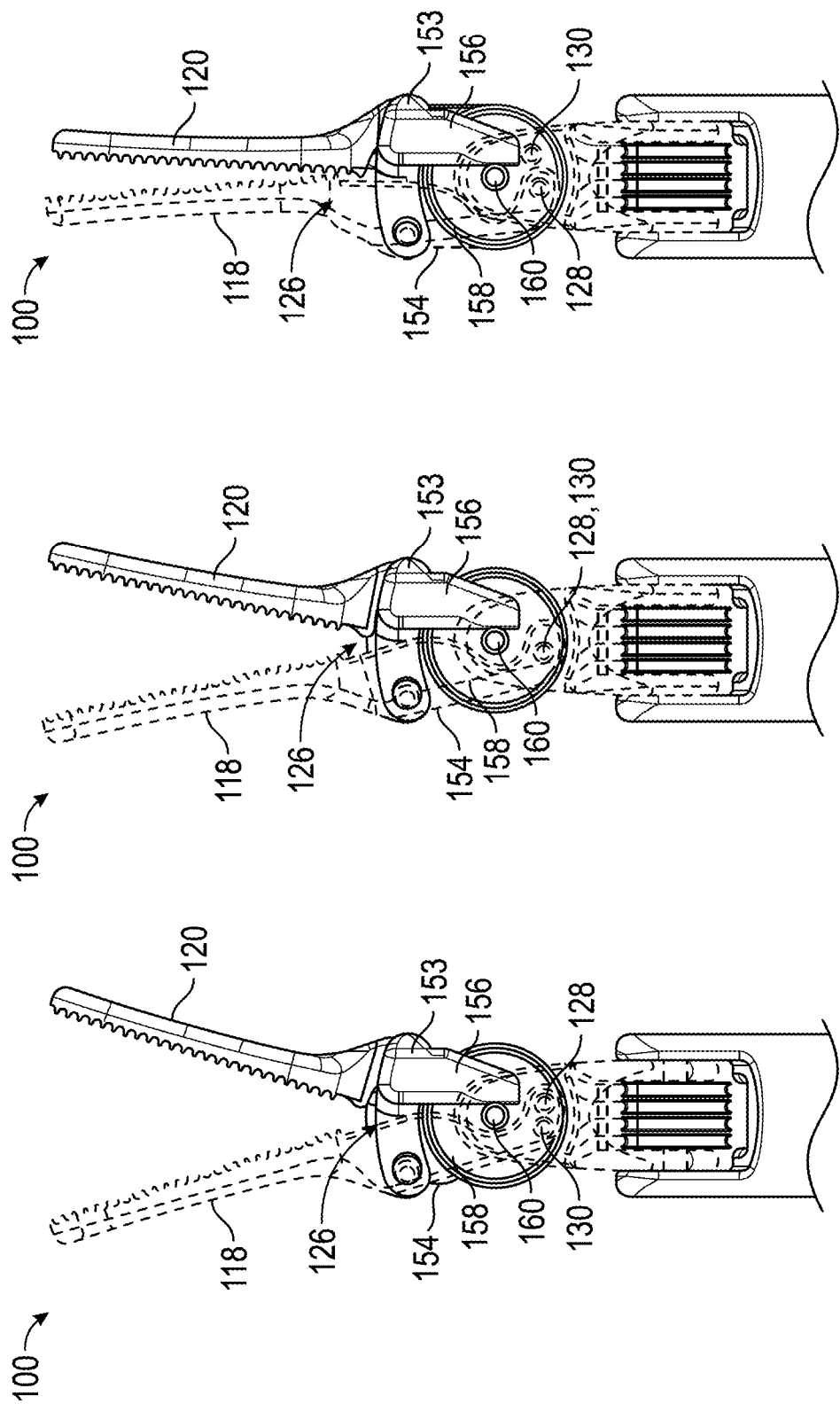

US 10,751,140 B2

ROBOTIC MEDICAL SYSTEMS WITH HIGH FORCE INSTRUMENTS

PRIORITY APPLICATION

This application claims priority to U.S. Provisional Application No. 62/682,049, filed Jun. 7, 2018, which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application relates to robotic medical systems, and in particular, to robotic medical systems with high force instruments.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the instrument and an end effector thereof. The robotically-enabled medical system may include a robotic arm, or other instrument positioning device. The robotically-enabled medical system may also include a controller used to control the instrument during the procedure.

SUMMARY

In a first aspect, a robotic system includes an instrument having an end effector. The instrument comprises a first pulley configured to rotate about a pulley axis, a first jaw member connected to the first pulley by a first drive pin, a second pulley configured to rotate about the pulley axis, a second jaw member connected to the second pulley by a second drive pin, and a link providing a first pivot point about which the first jaw member can pivot and a second pivot point about which the second jaw member can pivot.

The robotic system may further include one or more of the following features in any combination: (a) a robotic arm coupled to the instrument; (b) wherein rotation of the first pulley causes rotation of the first drive pin about the pulley axis, further causing the first jaw member to pivot about the first pivot point, and rotation of the second pulley causes rotation of the second drive pin about the pulley axis, further causing the second jaw member to pivot about the second pivot point; (c) a geared constraint configured to constrain motion of the first jaw member and the second jaw member such that motion of one of the first jaw member and the second jaw member causes a substantially corresponding motion of the other of the first jaw member and the second jaw member; (d) wherein the geared constraint comprises a cycloid constraint, the cycloid constraint comprising a tooth formed on one of the first jaw member and the second jaw member, and a notch formed on the other of the first jaw member and the second jaw member; (e) wherein the geared constraint comprises a pin which extends along an axis through the first jaw member and the second jaw member, wherein the pin is configured to ride within a slot formed in at least one of the first jaw member and the second jaw member; (f) a slot constraint configured to prevent or reduce a risk of rotation of the end effector about the first drive pin and the second drive pin when the first drive pin and the second drive pins are aligned; (g) wherein the slot constraint comprises a first ear, a second ear spaced apart from the first ear to form a slot between the first ear and the second ear, and a pin extending along the pulley axis positioned within the slot; (h) wherein the first ear and the second ear are each coupled to the link; (i) a geared constraint configured to constrain motion of the first jaw member and the second jaw member such that motion of one of the first jaw member and the second jaw member causes a substantially corresponding motion of the other of the first jaw member and the second jaw member, and a slot constraint configured to prevent or reduce a risk of rotation of the end effector about the first drive pin and the second drive pin when the first drive pin and the second drive pins are aligned; (j) wherein the first pulley and the second pulley can rotate to a position in which the first drive pin and second drive pin are aligned; (k) wherein, during rotation of the first pulley and the second pulley, the first drive pin can rotate past the second drive pin; (l) wherein the link comprises a housing comprising a first bearing surface spaced apart from a second bearing surface, the first jaw member comprises a first groove configured to pivot on the first bearing surface to form the first pivot point, and the second jaw member comprises a second groove configured to pivot on the second bearing surface to form the second pivot point; (m) wherein the end effector is configured as a grasper, cutter, or clipper; (n) wherein a first link comprises a first distance between the pulley axis and a point at which an input force is applied by a cable wound on the first pulley, a second link comprises a second distance between the pulley axis and an axis of the first drive pin, a third link comprises a third distance between the axis of the first drive pin and an axis of the first pivot point, a fourth link comprises a fourth distance between the axis of the first pivot point and a distal end of the first jaw member; (o) wherein the first distance of the first link is between 3 and 4 mm, the second distance of the second link is between 2 and 3 mm, the third distance of the third link is between 7 and 8 mm, and the fourth distance of the fourth link is between 17 and 23 mm; (p) wherein the first distance of the first link is approximately 3.35 mm, the second distance of the second link is approximately 2.5 mm, the third distance of the third link is approximately 7.3 mm, and the fourth distance of the fourth link is approximately 20 mm; (q) wherein a first ratio between the second distance of the second link and the first distance of the first link is between 0.5 and 1.25, a second ratio between the third distance of the third link and the first distance of the first link is between 1.5 and 3.5, and a third ratio between the fourth distance of the fourth link and the first distance of the first link is between 1.5 and 20; and/or (r) wherein a first ratio between the second distance of the second link and the first distance of the first link is approximately 0.75, a second ratio between the third distance of the third link and the first distance of the first link is approximately 2.18, and a third ratio between the fourth distance of the fourth link and the first distance of the first link is approximately 6.

In another aspect, a robotic system includes a medical instrument comprising an end effector configured to be inserted into a patient during a medical procedure. The medical instrument comprises a first pulley, a first jaw member connected to the first pulley, a second pulley, a second jaw member connected to the second pulley, a link providing a first pivot point about which the first jaw member can pivot and a second pivot point about which the second jaw member can pivot, and at least one of a geared constraint and a slot constraint.

The robotic system may further include one or more of the following features in any combination: (a) wherein the end effector is connected to a robotic arm and controlled by a processor of the system; (b) wherein the end effector and at least a portion of the medical instrument are configured to fit through a patient opening that is less than 14 mm; (c) wherein the end effector and at least a portion of the medical instrument are configured to fit through a patient opening that is less than 10 mm; (d) wherein the end effector and at least a portion of the medical instrument are configured to fit through a patient opening that is less than 10 mm; (e) wherein the end effector is connected to the distal end of the medical instrument by a wrist having at least two degrees of freedom; (f) one or more cables connected to the first pulley, wherein pulling one or more of the cables connected to the first pulley causes rotation of the first pulley, and one or more cables connected to the second pulley, wherein pulling one or more cables connected to the second pulley causes rotation of the second pulley; (g) wherein the one or more of the cables connected to the first pulley and the one or more of the cables connected to the second pulley extend through the medical instrument, the medical instrument is attached to an instrument drive mechanism, and the instrument drive mechanism is configured to pull the one or more of the cables connected to the first pulley and the one or more of the cables connected to the second pulley to actuate the end effector; (h) wherein the end effector comprises the geared constraint, wherein the geared constraint comprises a cycloid constraint that is configured to constrain motion of the first jaw member and the second jaw member such that motion of one of the first jaw member and the second jaw member causes a substantially corresponding motion of the other of the first jaw member and the second jaw member; (i) wherein the geared constraint comprises a tooth formed on one of the first jaw member and the second jaw member, and a notch formed on the other of the first jaw member and the second jaw member; (j) wherein the end effector comprises the slot constraint, wherein the slot constraint is configured to prevent rotation of the end effector about the first drive pin and the second drive pin when the first drive pin and the second drive pins are aligned; and/or (k) wherein the end effector comprises the slot constraint and the geared constraint.

In another aspect, a method includes inserting a robotically-controlled medical instrument into a patient. The instrument including an end effector. The end effector comprises (i) a first jaw member coupled to a first pulley, (ii) a second jaw member coupled to a second pulley, (iii) a link connecting the first jaw member and the second member, and (iv) at least one of a geared constraint and a slot constraint; and actuating the end effector based on pulling at least one cable connected to the first pulley or the second pulley to cause rotation of the first pulley or the second pulley, wherein rotation of the first pulley or the second pulley opens or closes the first jaw member and the second jaw member of the end effector.

The method may further include one or more of the following features in any combination: (a) wherein actuating the end effector comprises causing rotation of the first pulley and the second pulley such that a first drive pin connecting the first pulley to the first jaw member overlaps with a second drive pin connecting the second pulley to the second drive; (b) wherein the overlap of the first drive pin and the second drive pin increases force amplification at the end effector; (c) wherein the end effector comprises the geared constraint, and wherein the geared constraint is configured to constrain motion of the first jaw member and the second jaw member such that motion of one of the first jaw member and the second jaw member causes a substantially corresponding motion of the other of the first jaw member and the second jaw member; (d) wherein the geared constraint comprises a cycloid constraint comprising a tooth formed on one of the first jaw member and the second jaw member, and a notch formed on the other of the first jaw member and the second jaw member; (e) wherein the end effector comprises the slot constraint, wherein the slot constraint is configured to prevent rotation of the end effector about the first drive pin and the second drive pin when the first drive pin and the second drive pins are aligned; and/or (f) wherein the end effector comprises the slot constraint and the geared constraint.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 18A illustrates another embodiment of a high force instrument in an open position.

FIG. 18B illustrates the high force instrument of FIG. 18A in a closed position.

FIGS. 24A-24H illustrate views of an embodiment of a high force instrument that includes two constraints. FIG. 24A is a front view of the instrument in an open position, FIG. 24B is an exploded view of the instrument, FIG. 24C is a side view of the instrument, FIG. 24D is a back view of the instrument in an open position, and FIG. 24E is a bottom cross-sectional view of the instrument. FIGS. 24F, 24G, and 24H illustrate drive pins crossing as the instrument moves from an open position to a closed position.

FIGS. 25A and 25B illustrate views of the instrument in open and closed configurations, respectively. FIG. 25C illustrates an embodiment of a housing that serves as the link for the instrument. FIG. 25D illustrates a view of a first or second jaw member for the instrument. FIGS. 25E, 25F, 25G, and 25H illustrate stages during an example assembly process for the instrument.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
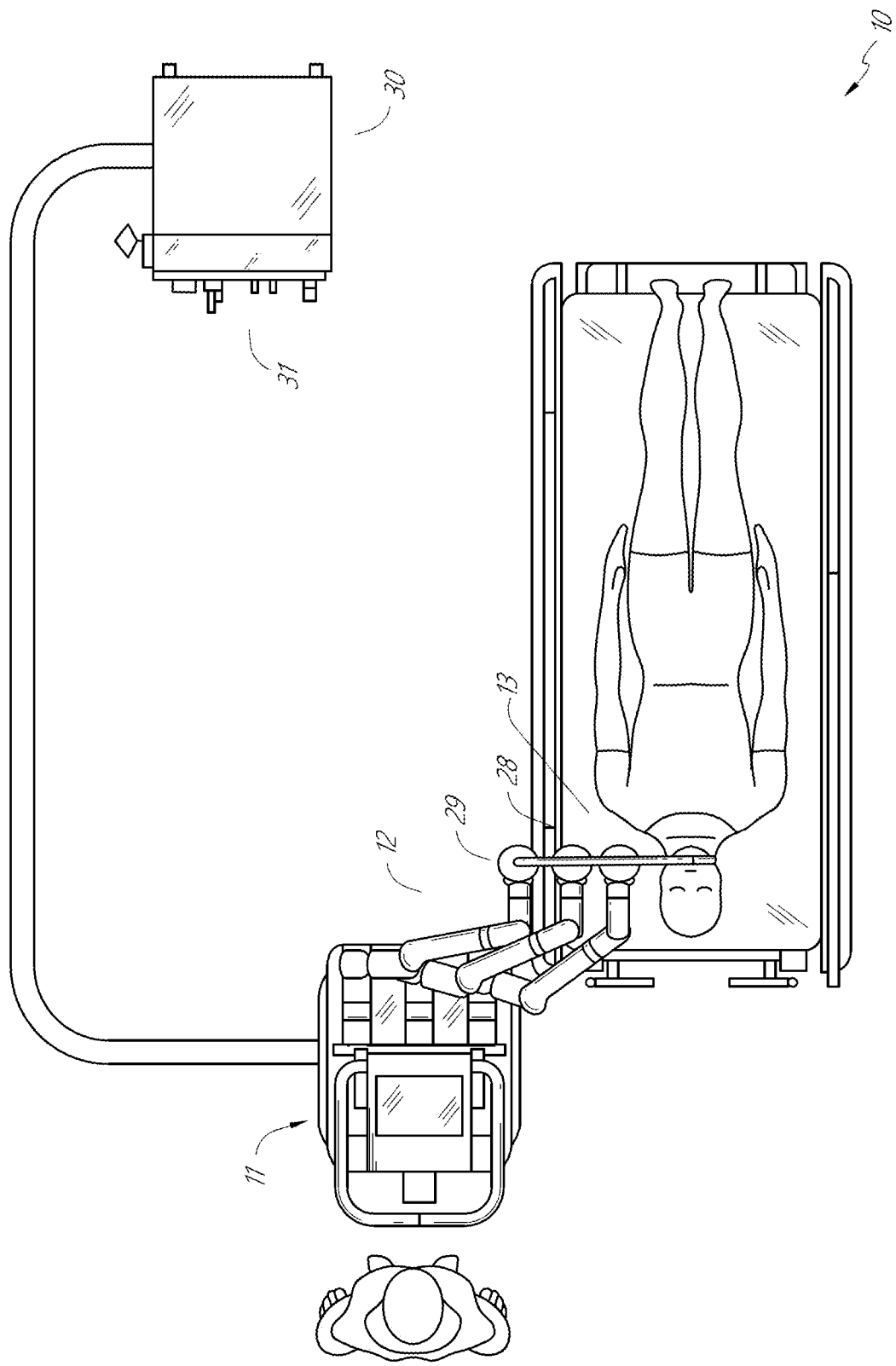
FIG. 1 illustrates an embodiment of a cart-based robotic system arranged for diagnostic and/or therapeutic bronchoscopy.
Figure 2:
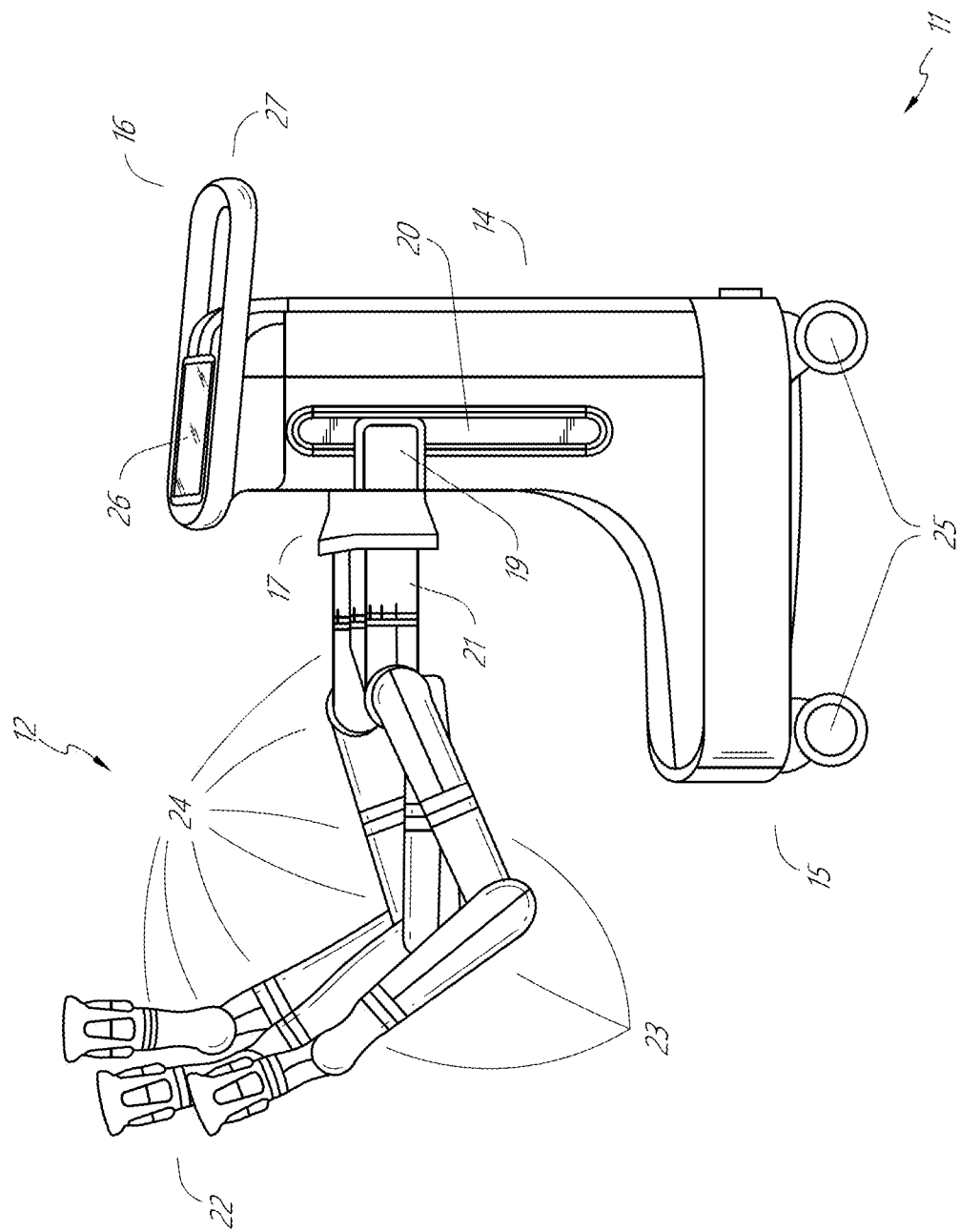
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both pre-operative and intraoperative data. Potential pre-operative data on the touchscreen 26 may include pre-operative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
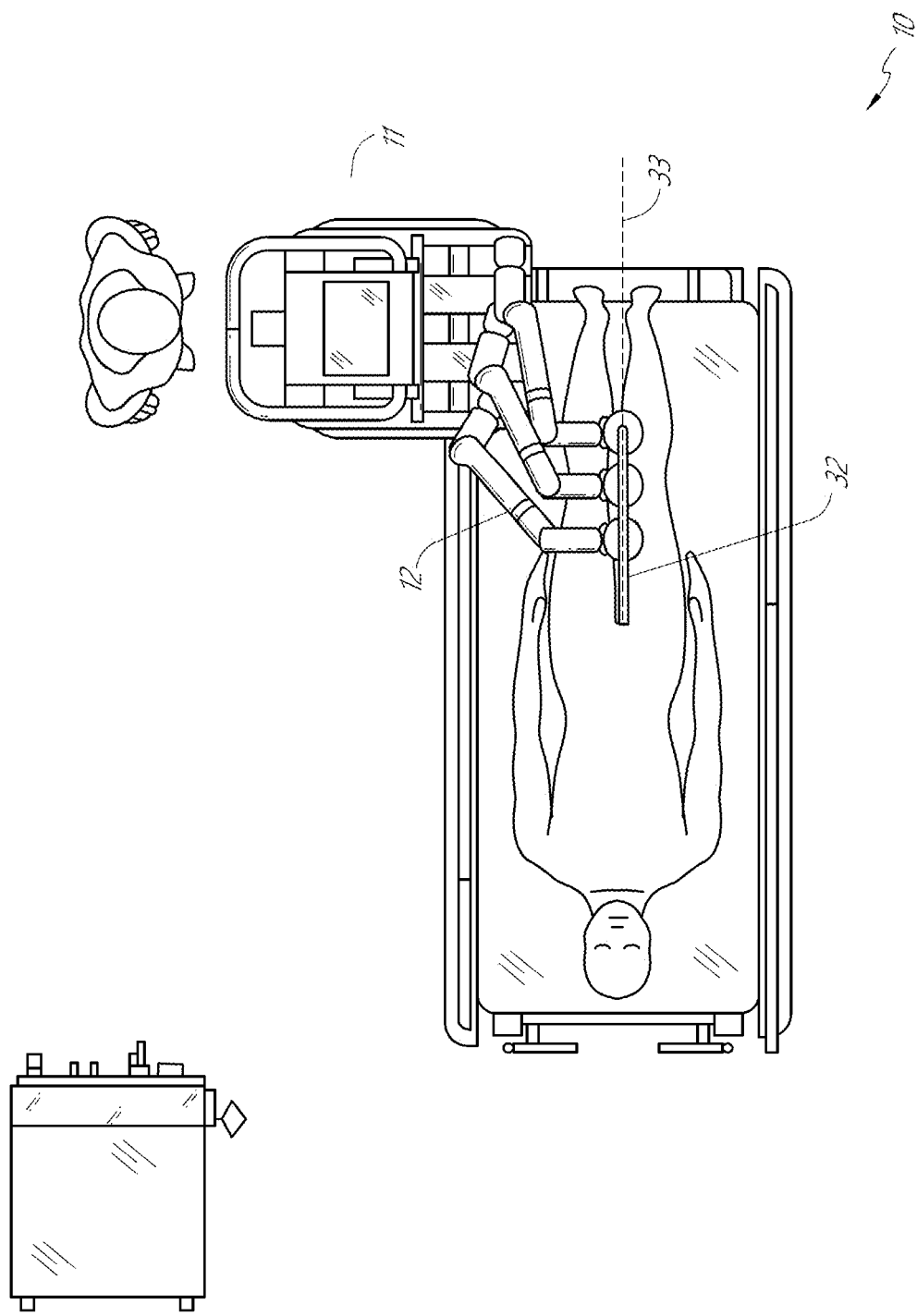
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
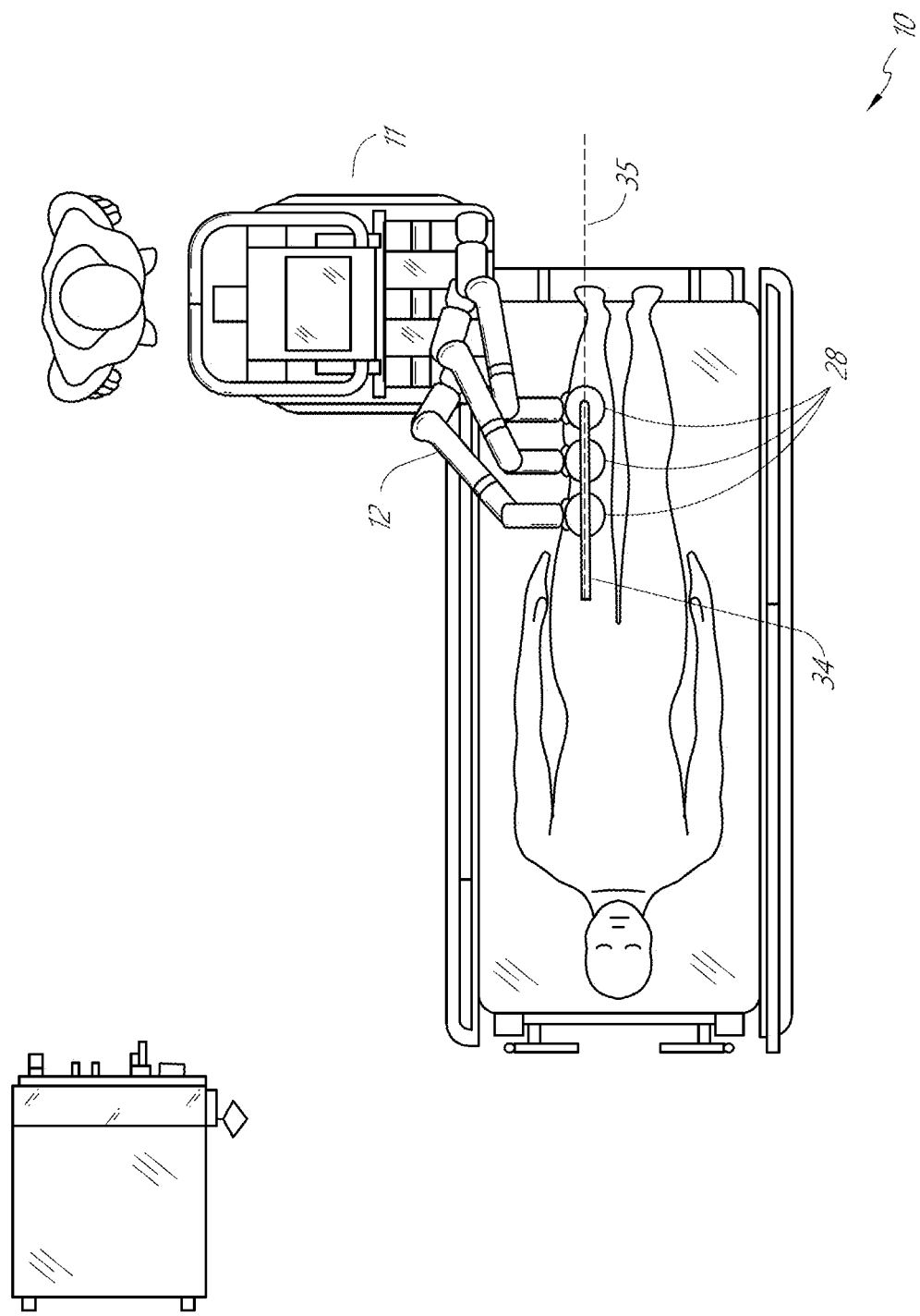
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
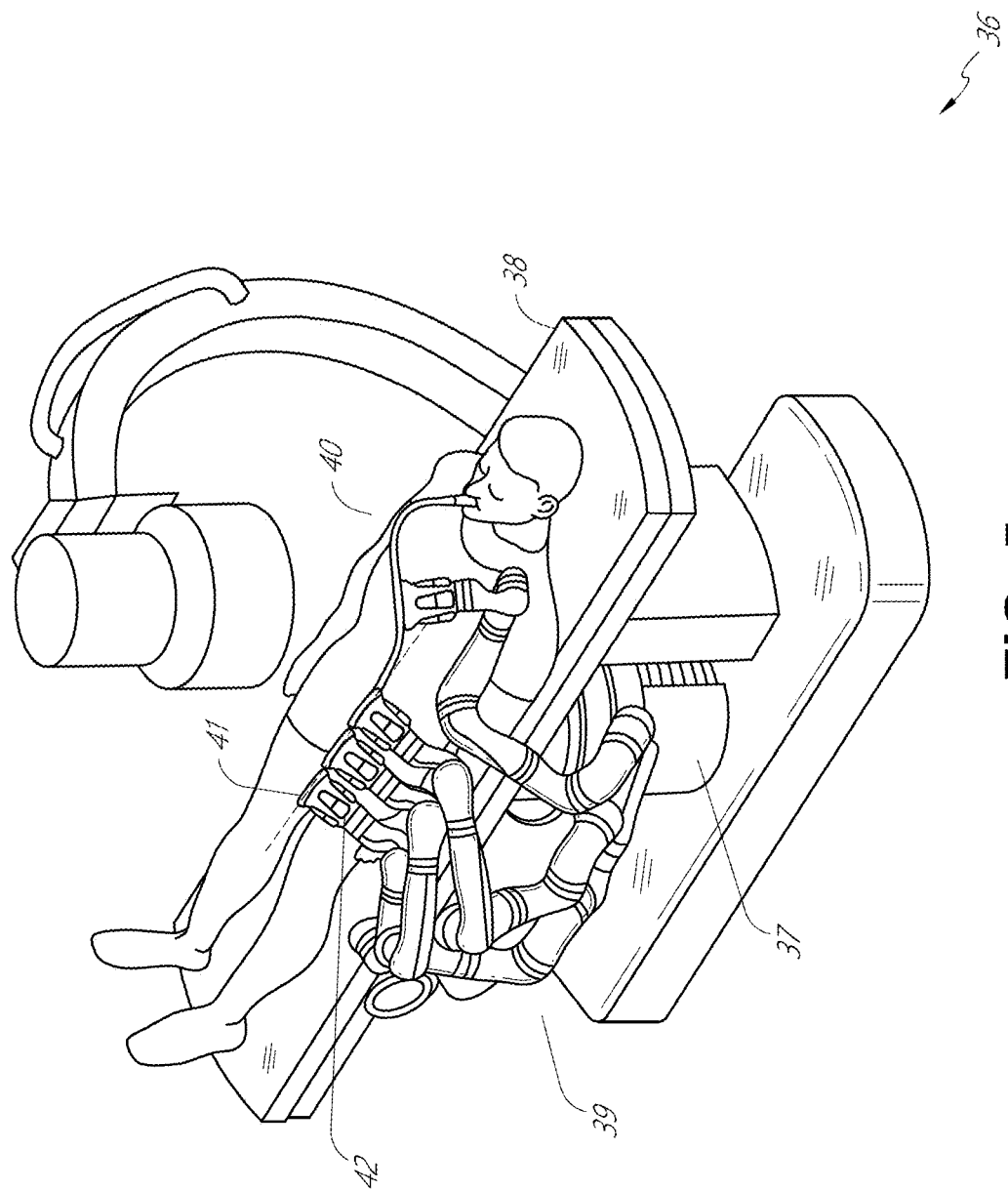
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
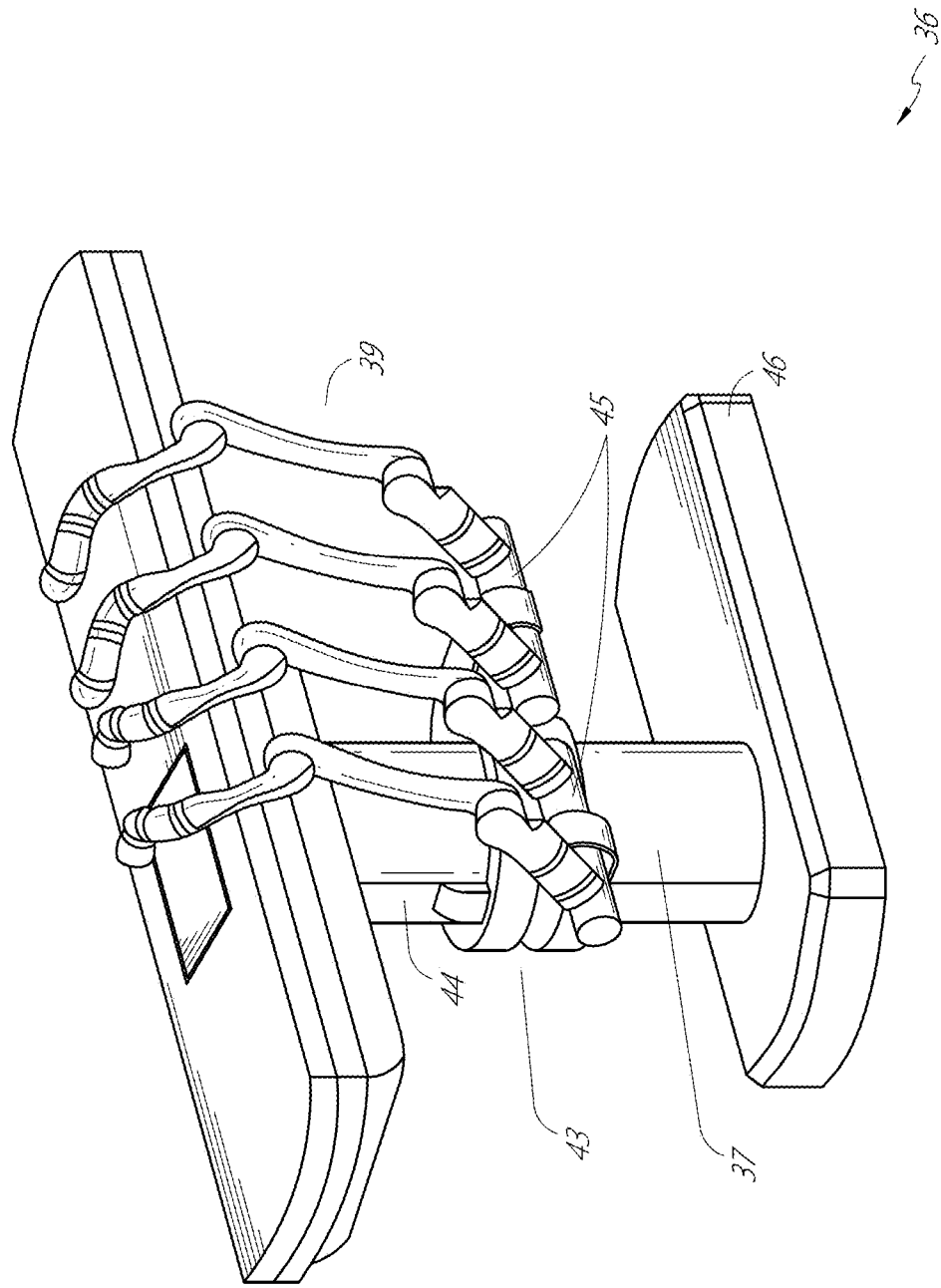
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
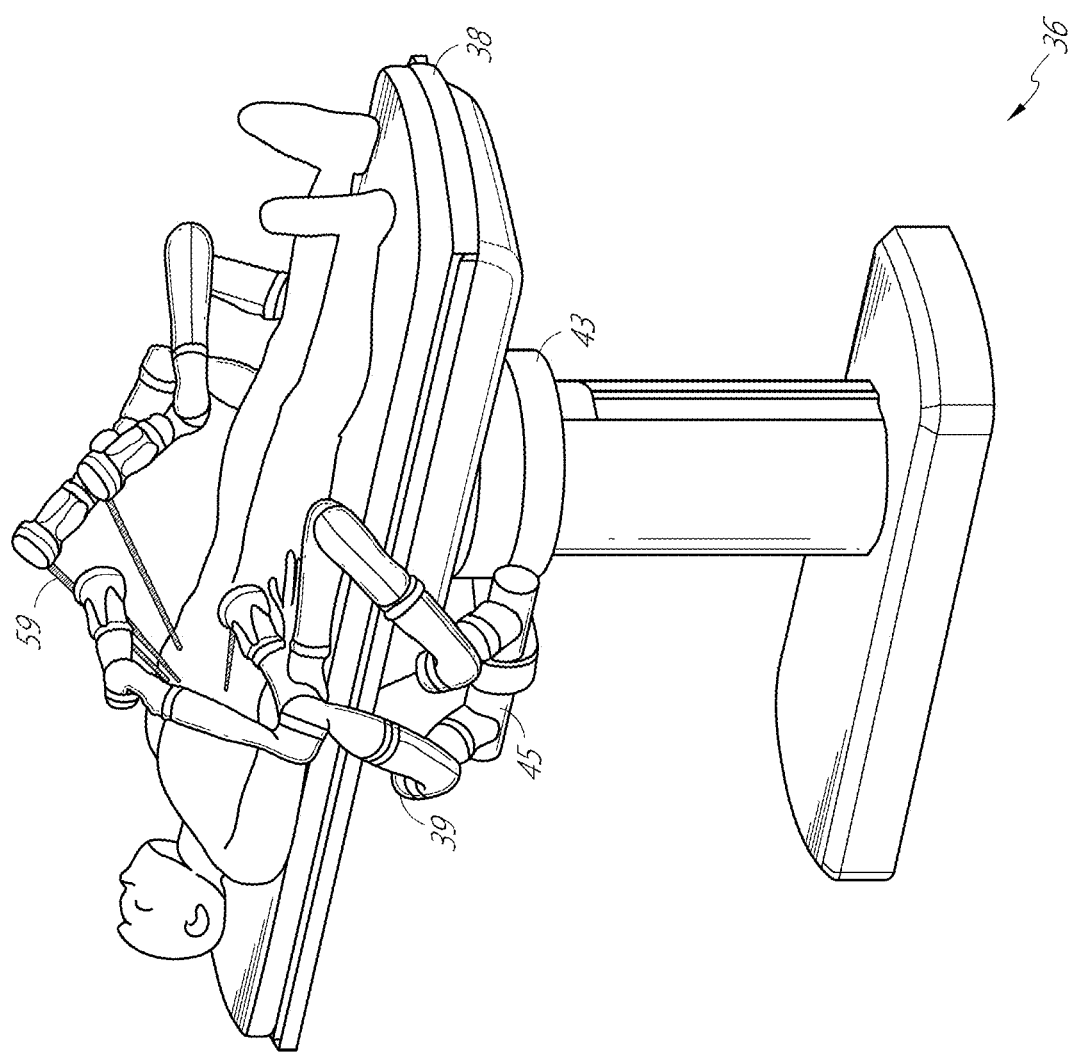
FIG. 9 illustrates an embodiment of a table-based robotic system configured for a laparoscopic procedure.

The robotic arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages based the lead screws. The column 37 may also convey power and control signals to the carriages 43 and the robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
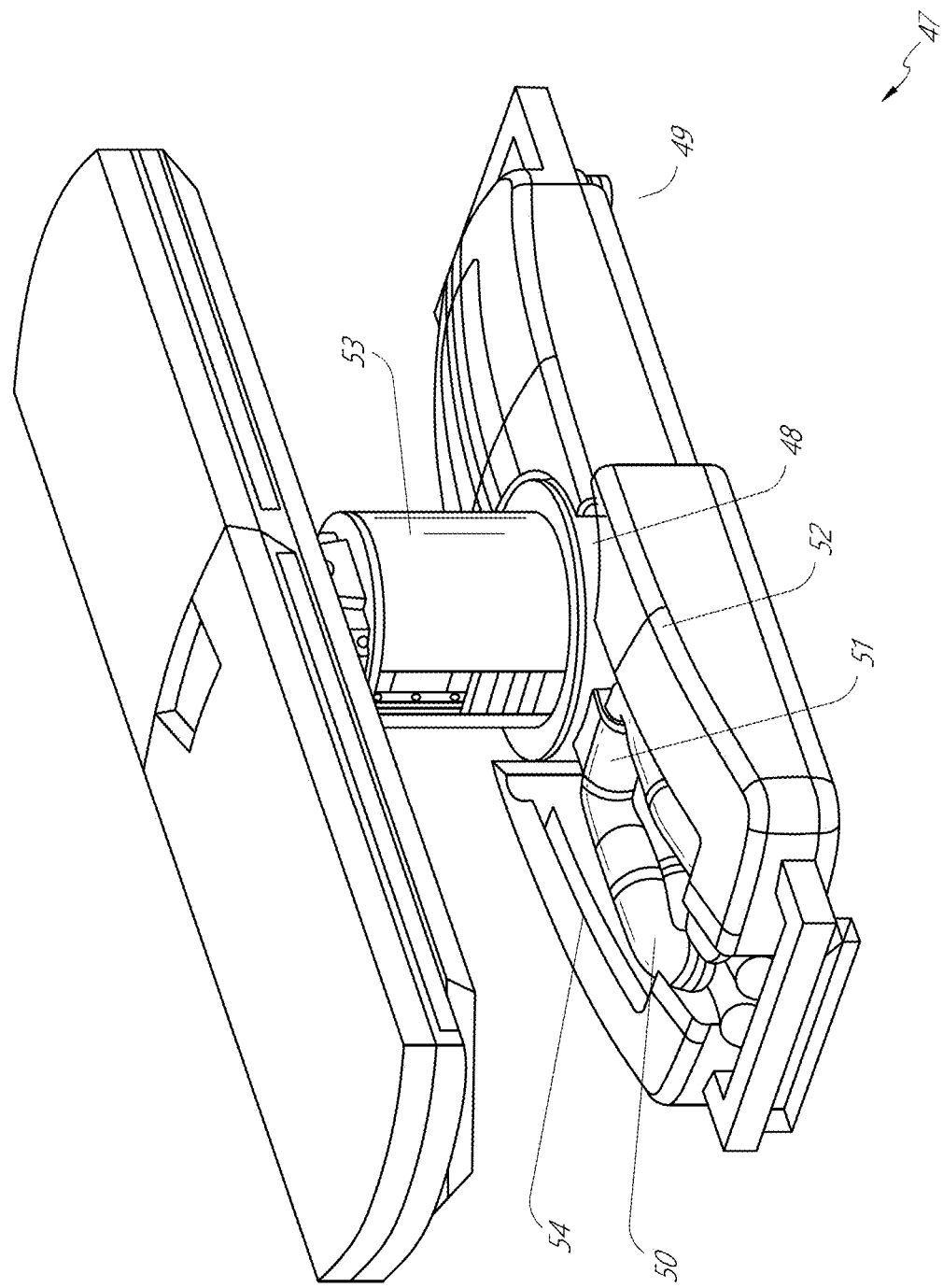
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
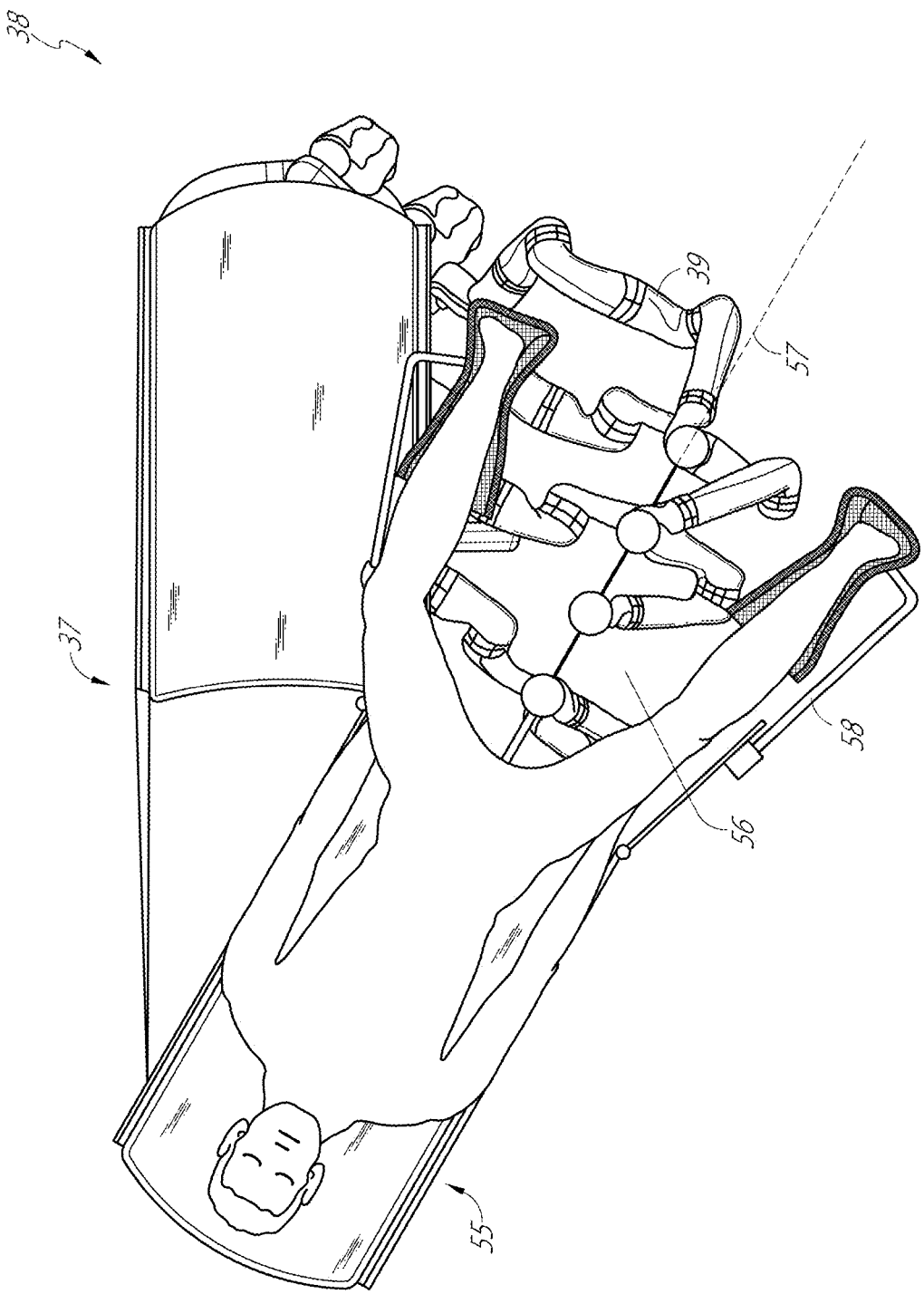
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
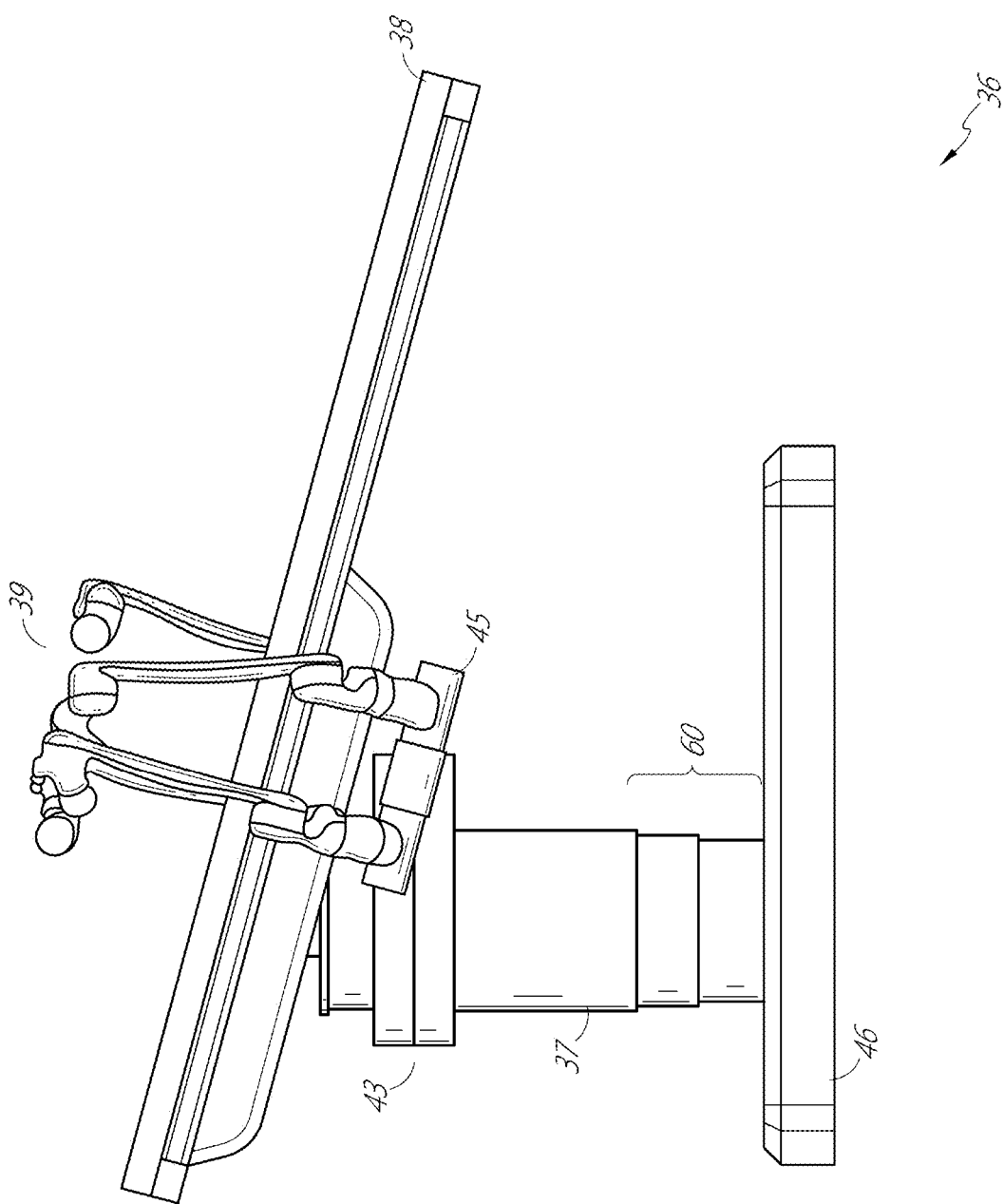
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
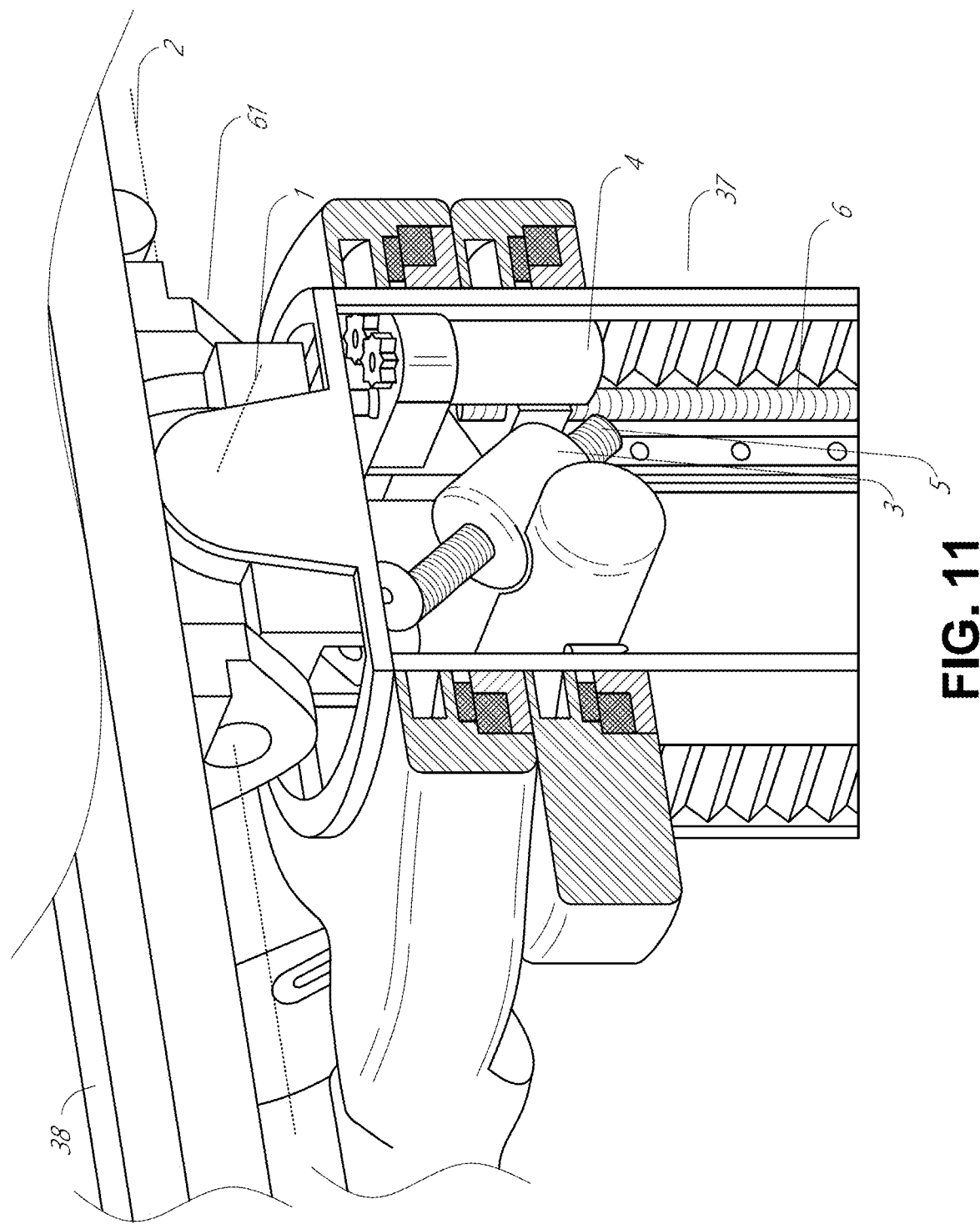
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
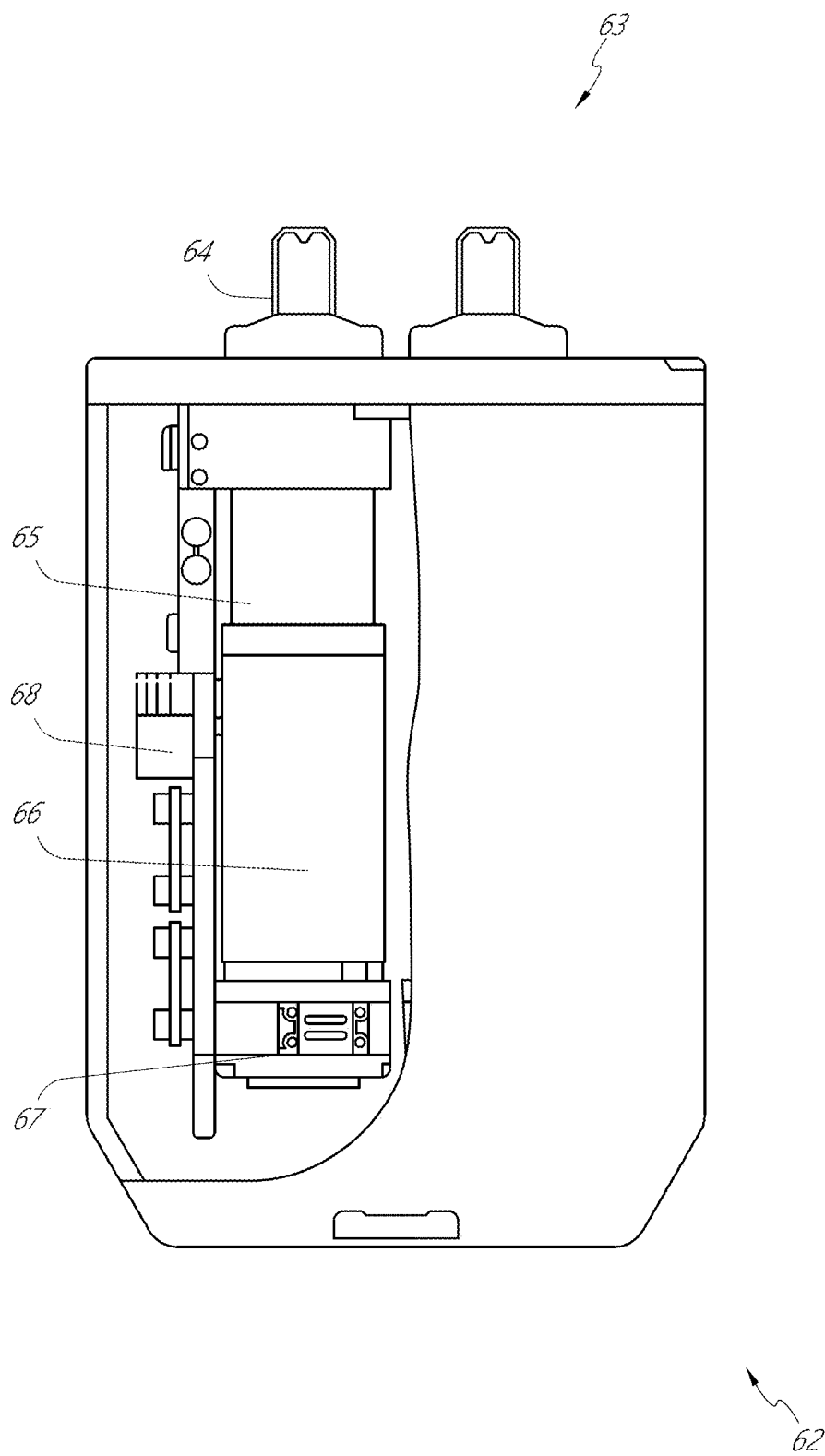
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
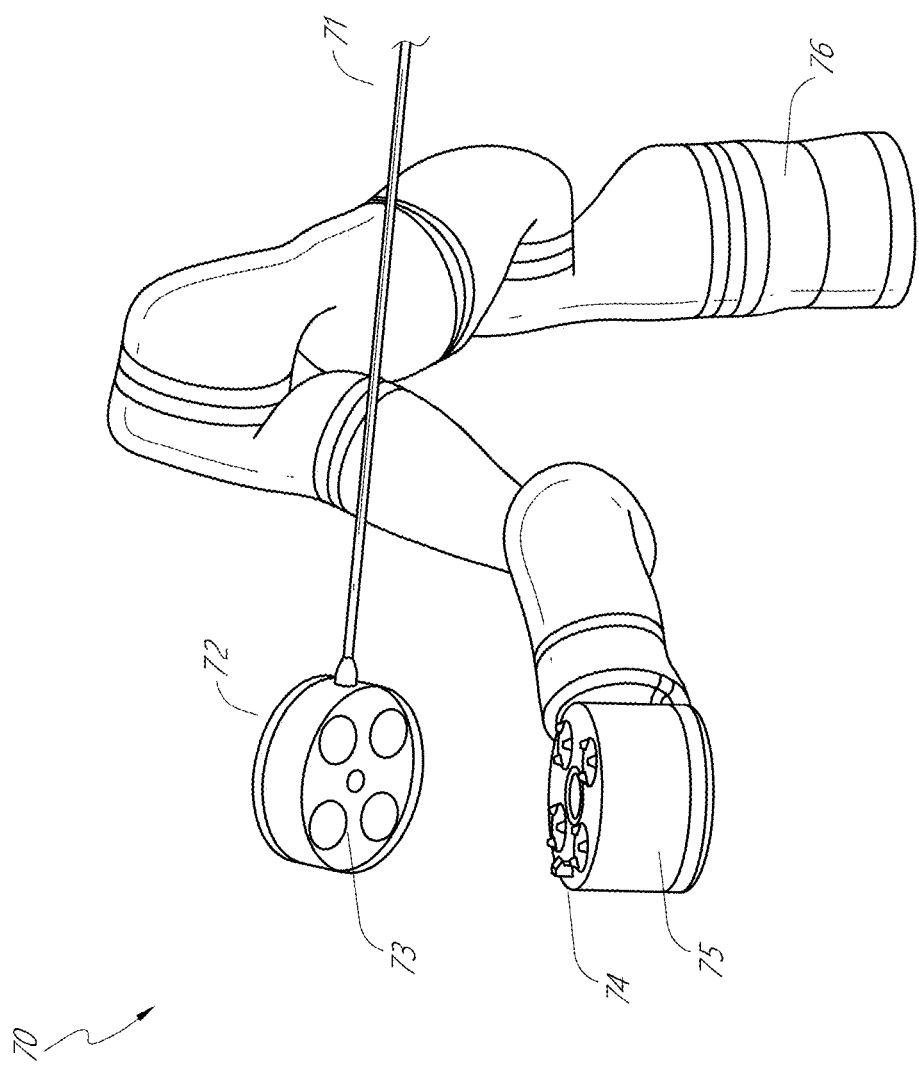
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 14:
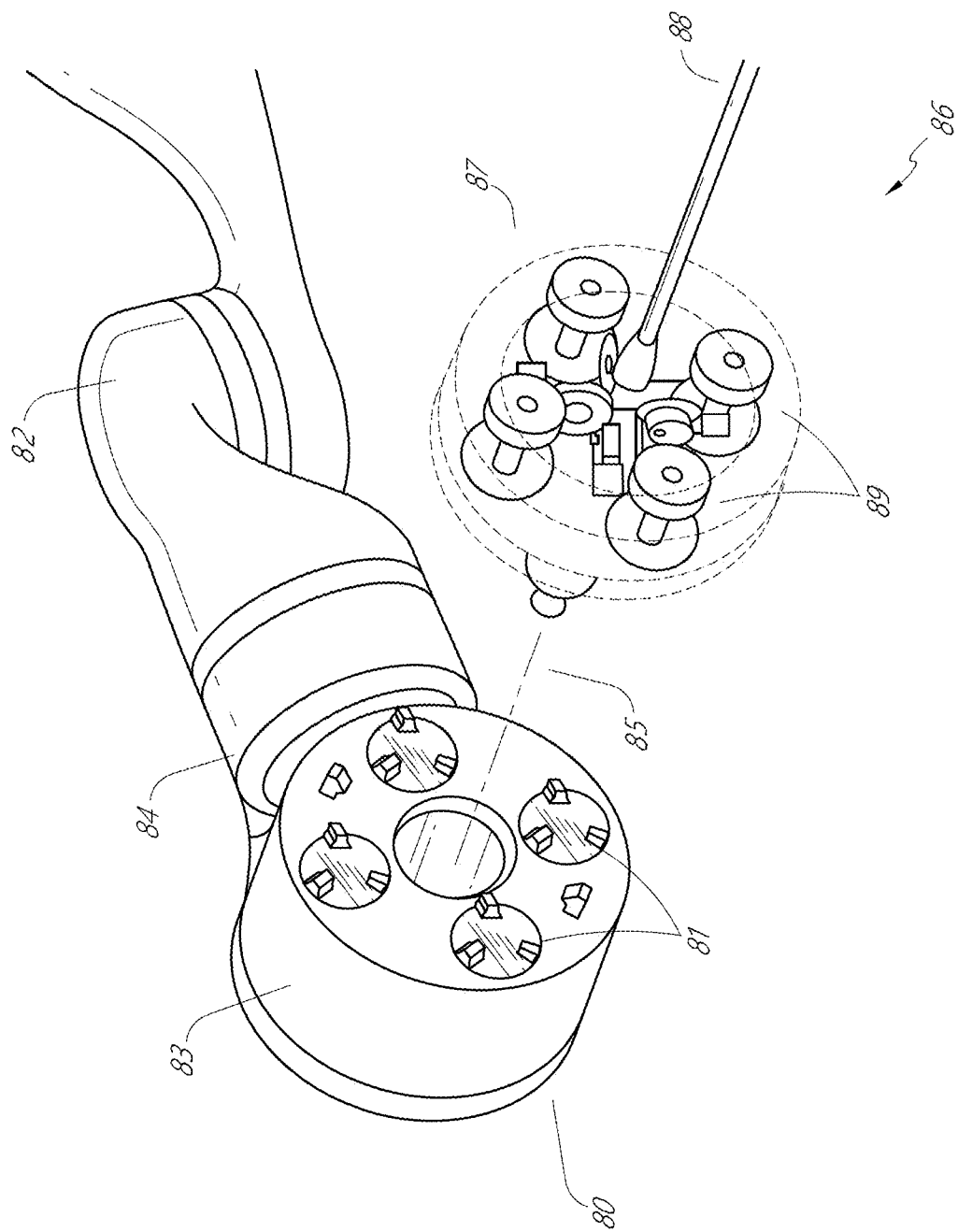
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 15:
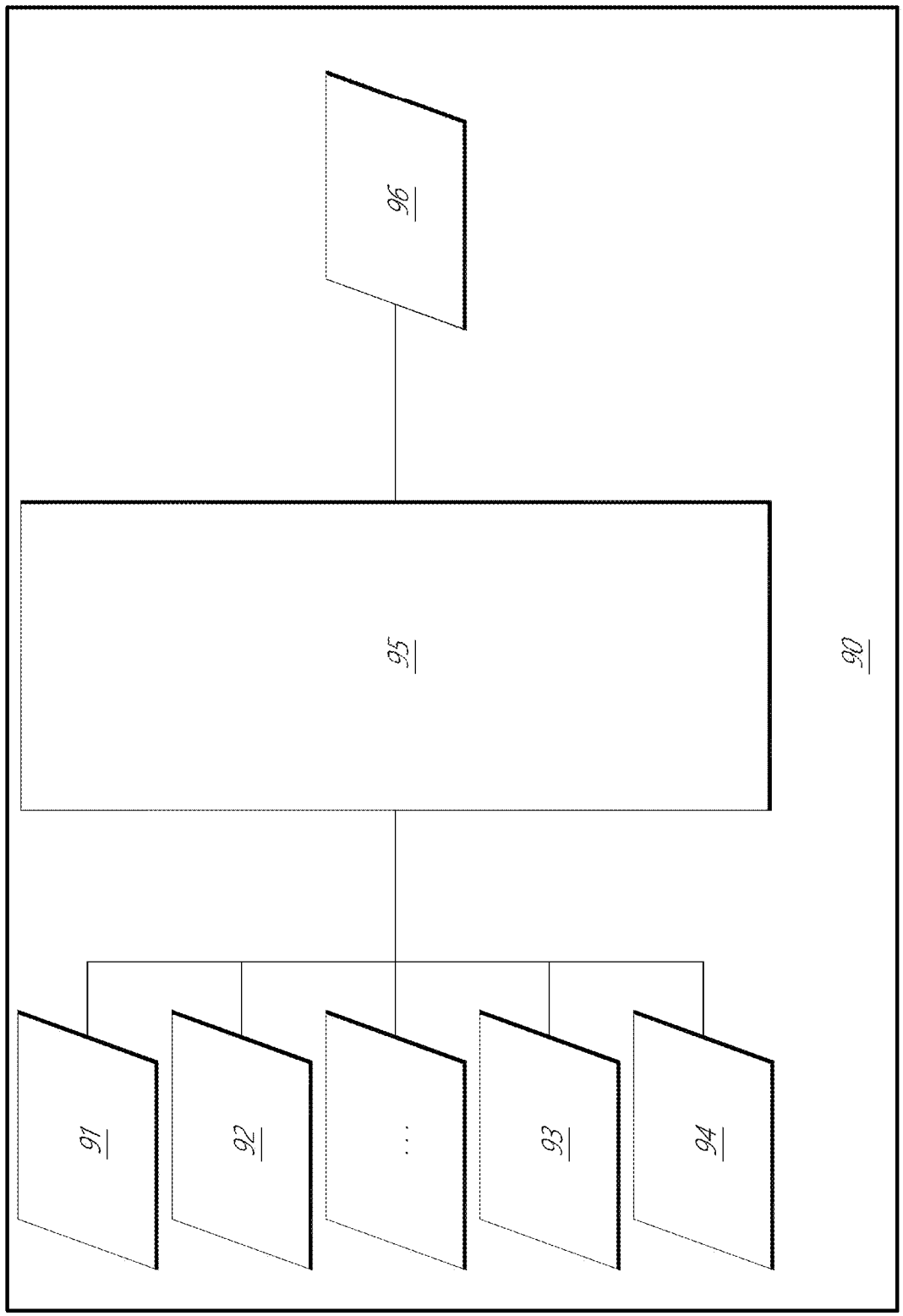
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image) 92. The localization module 95 may process the vision data to enable one or more vision-based (or image-based) location tracking modules or features. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Robotically-Enabled Medical Systems with High Force Instruments

Robotically-enabled medical systems, such as the systems described above, can include high force instruments as described in this section. As used herein, a high force instrument can refer to an instrument including an end effector (such as a grasper, gripper, cutter, etc.) that is configured to generate a mechanical advantage whereby inputs are amplified by the structure of the instrument to produce amplified outputs. In some embodiments, force inputs are amplified to produce force outputs that are greater than the force inputs. For example, in some embodiments, a high force instrument includes an end effector configured as a grasper, and the high force instrument is configured such that input forces (e.g., forces applied on pull wires of the instrument) are amplified such that output forces at the jaws of the grasper are greater than the input forces. In some embodiments, the high force instrument includes a novel structure that provides a mechanical advantage that can achieve even greater output than without the mechanical advantage. In some embodiments, the high force instruments are robotically controlled instruments as described above.

In many of the examples described herein, the end effectors of the high force instruments are actuated with pull wires. The pull wires may be wrapped around pulleys within the instrument. In some embodiments, the high force instruments are capable of outputting a higher force than a simple pulley drive in a wrist configuration. For example, a high force instrument may provide a mechanical advantage of two to one, three to one, four to one, five to one, or ten to one. Other mechanical advantages are also possible.

In many of the embodiments described below and illustrated in the figures, the high force instrument is a high force grasper. However, the mechanisms described herein that are configured to obtain a high force can be applied to other types of instruments as well, including clipping and cutting instruments, among others.

A. Example Instruments with High Force End Effectors

Figure 16A:
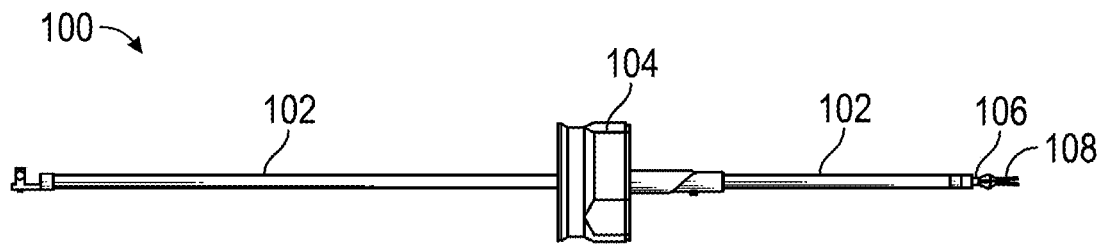
FIG. 16A illustrates a side view of a high force instrument.

FIG. 16A illustrates a side view of an embodiment of a high force instrument 100. As will be discussed below, the instrument 100 can be configured to provide a mechanical advantage that can, for example, amplify input forces to produce increased output forces. In the illustrated embodiment, the instrument 100 includes an elongated shaft 102 and a handle 104. The elongated shaft 102 extends between a distal end and a proximal end. An end effector 108, which in the illustrated embodiment is configured as a grasper, can be positioned at the distal end of the elongated shaft 102. In some embodiments, for example, as illustrated, the end effector 108 is connected to the distal end of the elongated shaft 102 by a wrist 106. The wrist 106 can be configured to allow one or more degrees of freedom for the instrument 100. For example, the wrist 106 can be a two degree-of-freedom wrist. As an example, a two degree-of-freedom wrist can allow the end effector 108 to pivot or rotate around a pitch axis and a yaw axis. In some embodiments, the wrist 106 can be fixed, so as to provide zero degrees of freedom. In some embodiments, the wrist 106 may allow one, two, three, or more degrees of freedom. An example embodiment of a wrist 106 and end effector 108 are shown in greater detail in FIG. 16B, which is described further below.

As shown in FIG. 16A, in some embodiments, the instrument 100 includes the handle 104. The handle 104 can be configured to connect to an instrument drive mechanism, for example, as shown in FIGS. 13 and 14, which have been described above. As previously mentioned, the instrument 100 may include one or more tendons, cables, or pull wires that extend along (e.g., through or on) the elongated shaft 102 between the end effector 108 and the handle 104. The handle 104 may include one or more drive inputs configured to engage one or more drive outputs on the instrument drive mechanism (see FIG. 14) that allow the instrument drive mechanism to actuate (e.g., tension or pull) the pull wires. Actuating the pull wires can cause motion of the end effector 108 to allow for remote manipulation and control of the end effector 108. For example, in some embodiments, actuation of the pull wires can be configured to cause jaws of the end effector 108 to open and close and/or to allow the end effector 108 to rotate about pitch or yaw axes. As mentioned above, the instrument drive mechanism can be positioned on a robotic arm. In some embodiments, the robotic arm can be controlled to position, roll, advance, and/or retract the instrument 100.

As shown in FIG. 16A, in some embodiments, the elongated shaft 102 extends through the handle 104. In such an embodiment, the elongated shaft 102 can be configured to advance or retract relative to the handle 104. In some embodiments, the instrument drive mechanism is configured to cause the elongated shaft 102 to advance or retract relative to the handle 104. This can allow, for example, the handle 104 to remain stationary while the elongated shaft 102 and end effector 108 are advanced into a patient during a procedure. In some embodiments, the proximal end of the elongated shaft 102 is attached to the handle 104 such that the elongated shaft 102 extends only between the end effector 108 and the handle 104.

Figure 16B:
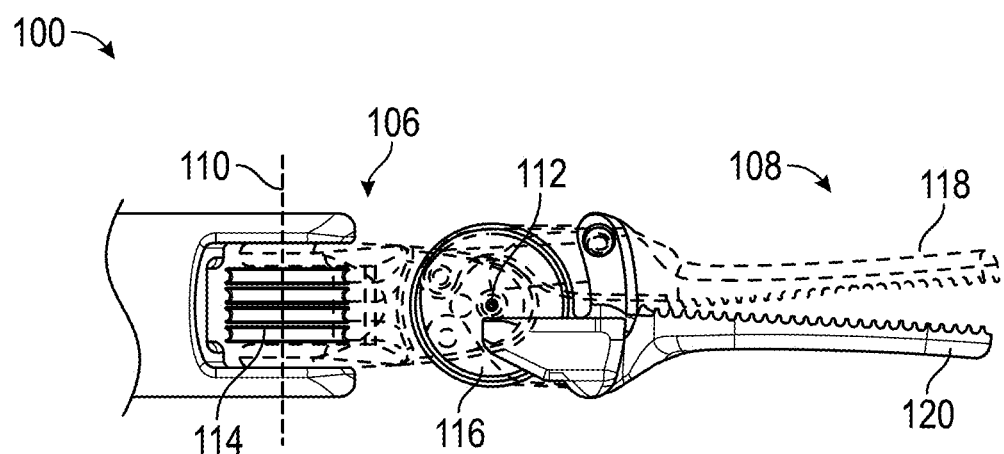
FIG. 16B illustrates a detailed view of a distal portion of the high force instrument of FIG. 16A, showing additional detail of a wrist and an end effector of the high force instrument.

FIG. 16B illustrates a detailed view of the distal end of the instrument 100 and shows an embodiment of the wrist 106 and the end effector 108. In the illustrated embodiment, the end effector 108 is configured as a grasper or gripper, although other types of end effectors (e.g., cutters or snippers) are possible. The end effector 108 includes a first grip or jaw member 118 and a second grip or jaw member 120. The angle between the jaw members 118, 120 can be controlled to operate the end effector 108. For example, the jaw members 118, 120 can be opened and closed.

In the illustrated embodiment, the wrist 106 is a two degree-of-freedom wrist, although as mentioned above, the wrist 106 can provide other numbers of degrees-of-freedom in other embodiments. The illustrated two degree-of-freedom wrist 106 is configured to allow the end effector 108 to pivot around a first axis 110 and a second axis 112. In the illustrated configuration, the second axis 112 extends into and out of the plane of the page. The first axis 110 and the second axis 112 can be orthogonal. In some embodiments, the first axis 110 can be a pitch axis and the second axis 112 can be a yaw axis for the instrument 100.

In some embodiments, the instrument 100 includes pulleys 114 and pulleys 116. In some embodiments, the pulleys 114 and/or the pulleys 116 can be considered part of the instrument 100, part of the wrist 106, and/or part of the end effector 108. As illustrated, the pulleys 114 are configured to rotate around the first axis 110 and the pulleys 116 are configured to rotate around the second axis 112. Although not illustrated, pull wires extending along the elongated shaft 102 can be positioned so as to engage with the pulleys 114 and the pulleys 116. The end effector 108 can be controlled (e.g., opened, closed, rotated about the first axis 110, and/or rotated about the second axis 112) depending upon which of the pull wires are actuated.

In some embodiments, the elongated shaft 102, wrist 106, and end effector 108 can be configured to be inserted into a patient during a minimally invasive procedure, such as a laparoscopic or endoscopic procedure. For example, in some embodiments, the elongated shaft 102, wrist 106, and end effector 108 are configured to be inserted through a small incision or other surgical port having a diameter or length of about 14 mm or less, about 12 mm or less, or about 10 mm or less. Thus, in some embodiments, a maximum diameter or thickness of the elongated shaft 102, wrist 106, and end effector 108 can be about or less than 14 mm, 12 mm, or 10 mm. Other sizes are also possible. The high force instruments described herein can also be used for non-minimally invasive procedures, such as open surgery.

Due to the narrowness of the elongated shaft 102, wrist 106, and end effector 108 (for example, so as to be useable for minimally invasive procedures), it can be difficult to provide a structure that configures the instrument 100 to provide a mechanical advantage. For example, the small diameter or thickness can limit the moment arms through which forces may be transmitted to distal gripping, clipping and cutting devices. With limited moment arms, it can be difficult to get an amplified output and mechanical advantage. However, as will be described in greater detail below (for example, with reference to FIGS. 17A-20D) the instruments 100 described herein can be configured to advantageously provide a mechanical advantage, while remaining suitable for minimally invasive procedures. For example, the instruments 100 can include a distal force amplification mechanism that may allow higher gripping and cutting forces at lower actuation forces while maintaining a small overall diameter for the instrument 100. Various features of the instrument 100 that configure the instrument 100 to provide a mechanical advantage will now be described with reference to FIGS. 17A-20D.

Figure 17A:
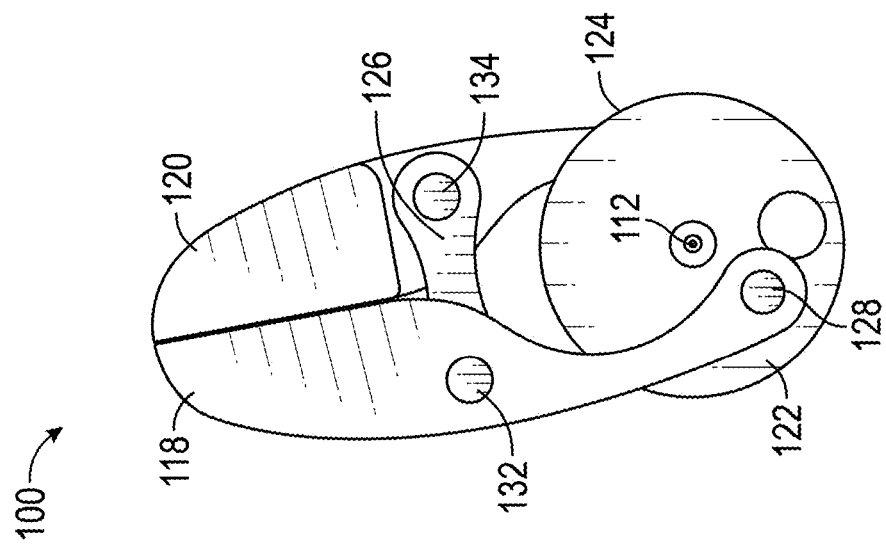
FIG. 17A illustrates an embodiment of a high force instrument in an open position.
Figure 17B:
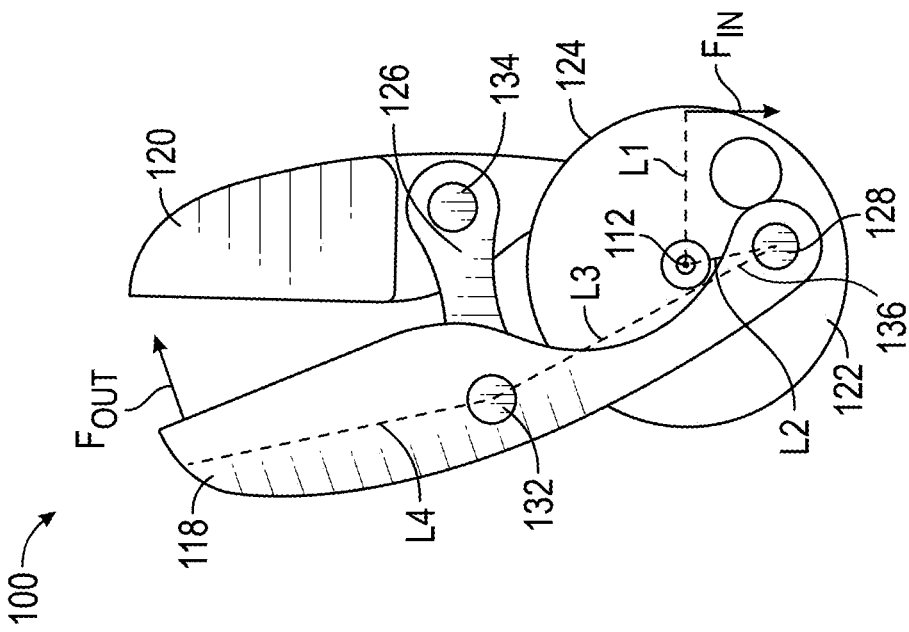
FIG. 17B illustrates the high force instrument of FIG. 17A in a closed position.

FIGS. 17A and 17B illustrate components of an embodiment of the high force instrument 100 configured to provide a mechanical advantage. FIG. 17A illustrates the instrument 100 in an open position, and FIG. 17B illustrates the instrument 100 in a closed position. In this embodiment, the instrument 100 includes a first jaw member 118, a second jaw member 120, a first pulley 122, a second pulley 124 (behind the first pulley 122), and a link 126 arranged to provide a mechanical advantage. The first pulley 122 and the second pulley 124 can be the pulleys 116 mentioned above.

As illustrated, a proximal end of the first jaw member 118 is connected to the first pulley 122. The proximal end of the first jaw member 118 can be connected to the first pulley 122 by a first drive pin 128. The first drive pin 128 may be integrally formed with the first jaw member 118 or the first pulley 122, or may be a separate component (e.g., a rod extending through an opening in both the first jaw member 118 and the first pulley 122). Although not visible in FIGS. 17A and 17B, the proximal end of the second jaw member 120 is connected to the second pulley 124. The proximal end of the second jaw member 120 can be connected to the second pulley 124 by a second drive pin 130 (not visible in FIGS. 17A and 17B, but see, for example, FIGS. 24F-24H). Similar to the first drive pin 128, the second drive pin 130 may be integrally formed with the second jaw member 120 or the second pulley 124, or may be a separate component (e.g., a rod extending through an opening in both the second jaw member 120 and the second pulley 124). The first and second drive pins 128, 130 can allow the first and second jaw members 118, 120 to rotate relative to the first and second pulleys 122, 124, respectively.

Opposite the proximal ends, distal ends of the first jaw member 118 and the second jaw member 120 can each be configured as a component of the end effector 108. For example, the distal ends of the first jaw member 118 and the second jaw member 120 can each be configured as a gripping jaw member, a grasping jaw member, a cutting jaw member, a clipping jaw member, etc. In some embodiments, the end effector 108 can comprise a combined end effector that serves multiple functions, such as gripping and cutting. In some embodiments, when the end effector 108 of the instrument 100 is actuated, distal ends of the first jaw member 118 and the second jaw member 120 can interact with (e.g., contact) each other when the end effector 108 is closed to provide the end effector function (e.g., gripping or cutting).

The instrument 100 can include the link 126. In some embodiments, the link 126 can be considered a constraint (e.g., a link constraint or bar constraint). The link 126 can be configured to provide a first pivot point (e.g., at first link pin 132) about which the first jaw member 118 can pivot and a second pivot point (e.g., at second link pin 134) about which the second jaw member 120 can pivot to allow the end effector 108 to open and close. In some instances, the first and second pivot points can be referred to as dual pivots or dual pivot points. In the illustrated embodiment, the link 126 comprises a bar extending between the first jaw member 118 and the second jaw member 120, although in other embodiments, the link 126 may have a different configuration (for example, in the embodiment shown in FIGS. 25A-25H, the link 126 comprises a housing 190 that includes bearing surfaces 192, 194 that provide the pivot points).

In the illustrated embodiment, the link 126 is connected on a first end to the first jaw member 118 by a first link pin 132. The first link pin 132 may be integrally formed with the first jaw member 118 or the link 126, or may be a separate component (e.g., a rod extending through an opening in both the first jaw member 118 and the link 126). The first link pin 132 can be configured to allow the first jaw member 126 to rotate relative to the link 126. Similarly, the link 126 is connected on a second end to the second jaw member 120 by a second link pin 134. The second link pin 134 may be integrally formed with the second jaw member 120 or the link 126, or may be a separate component (e.g., a rod extending through an opening in both the second jaw member 120 and the link 126). The second link pin 134 can be configured to allow the second jaw member 126 to rotate relative to the link 126. Thus, in the illustrated embodiment, the link 126 provides a first pivot point at the first link pin 132 and a second pivot point at the second link pin 134.

The link 126 can be connected (for example, by the first and second link pins 132, 134) to the first and second jaw members 118, 120 between the proximal and distal ends of the first and second jaw members 118, 120. As will be discussed below, the position of the link 126, as well as the distance between the first and second pivot points, can be adjusted to vary the mechanical advantage provided by the instrument 100 (see, for example, FIGS. 20A-20D, described below).

As shown in FIGS. 17A, and 17B, for some embodiments, the first pulley 122 is configured to rotate around a pulley axis 112 (which may be the second axis 112 of FIG. 16B). In some embodiments, the pulley axis 112 is a central axis. In the illustrated embodiment, the pulley axis 112 extends into and out of the plane of the page. Similarly, the second pulley 124 is configured to rotate around the pulley axis 112.

In some embodiments, the axes of the first pulley 122 and the second pulley 124 can be substantially aligned. The first pulley 122 and the second pulley 124 can be configured such that each can rotate freely. That is, rotation of the first pulley 122 can be independent of rotation of the second pulley 124. For example, the first pulley 122 can rotate (e.g., clockwise or counterclockwise), while the second pulley 124 remains stationary (or vice versa), or the first pulley 122 can rotate in a first direction (e.g., either clockwise or counterclockwise), while the second pulley 124 rotates in a second direction (e.g. the other of clockwise or counterclockwise).

The first drive pin 128 can connect to or be positioned on the first pulley 122 at a radius or distance 136 (illustrated as a dashed line in FIG. 17A) from the pulley axis 112. Although not visible in FIGS. 17A and 17B, the second drive pin 130 can connect to or be positioned on the second pulley 124 at a radius or distance 136 from the pulley axis 112. In some embodiments, the distance 136 for the first pulley 122 can be equal to the distance 136 for the second pulley 124, although this need not be the case in all embodiments. As will be discussed below, the distance 136 can be adjusted to vary the mechanical advantage provided by the instrument 100 (see, for example, FIGS. 20A-20D, described below).

One or more pull wires can be engaged with the first pulley 122 that can be actuated (e.g., pulled) to cause rotation of the first pulley 122 in either a clockwise or counterclockwise direction around the pulley axis 112. Similarly, one or more pull wires can be engaged with the second pulley 124 that can be actuated (e.g., pulled) to cause rotation of the second pulley 124 in either a clockwise or counterclockwise direction around the pulley axis 112. In some embodiments, the first and second pulleys 122, 124 are wrapped with pull wires in an a-wrap configuration, as shown for example, in FIG. 21 (described below).

As mentioned above, the pull wires can be pulled or tensioned to actuate the end effector 108 of the instrument 100. For example, considering first the first pulley 122 and the first jaw member 118, a pull wire engaged with the first pulley 122 can be actuated to cause the first pulley 122 to rotate about the pulley axis 112. Rotation of the first pulley 122 is transmitted to the first jaw member 118 through the first drive pin 128. For example, considering FIG. 17A, when the first pulley 122 is rotated in a clockwise direction, the first drive pin 128 causes the proximal end of the first jaw member 118 to move to the left (for example, towards the position shown in FIG. 17B). As the proximal end of the first jaw member 118 is moved by rotation of the first pulley 122, the first jaw member 118 pivots about the first pivot point provided by the link 126, which in the illustrated embodiment, is the first link pin 132. Continuing with the example where the first pulley 122 is rotated in a clockwise direction, this motion of the first jaw member 118 causes the distal end of the first jaw member 118 to move towards the distal end of the second jaw member (e.g., closing end effector 108 of the instrument 100, for example, to the position shown in FIG. 17B). Conversely, rotation of the first pulley 122 in the counterclockwise direction causes the proximal end of the first jaw member 118 to move to the right, which rotates the first jaw member 118 about the first pivot point in the opposite direction, causing the distal end of the first jaw member 118 to move away from the distal end of the second jaw member 120 (opening the end effector 108 of the instrument 100).

The second pulley 124 and the second jaw member 120 may provide a similar motion upon rotation of the second pulley 124. In many instances, the second pulley 124 is rotated in the opposite direction than the first pulley 122, although this need not always be the case. For example, a pull wire engaged with the second pulley 124 can be actuated to cause the second pulley 124 to rotate about the pulley axis 112. Rotation of the second pulley 124 is transmitted to the second jaw member 120 through the second drive pin 130. For example, when the second pulley 124 is rotated in the counterclockwise direction, the second drive pin 130 causes the proximal end of the second jaw member 120 to move to the right. As the proximal end of the second jaw member 120 is moved by rotation of the second pulley 124, the second jaw member 120 pivots about the second pivot point provided by the link 126, which in the illustrated embodiment, is the second link pin 134. Continuing with the example where the second pulley 124 is rotated in a counterclockwise direction, this motion of the second jaw member 120 causes the distal end of the second jaw member 120 to move towards the distal end of the first jaw member 118 (e.g., closing end effector 108 of the instrument 100, for example, to the position shown in FIG. 17B). Conversely, rotation of the second pulley 124 in the clockwise direction causes the proximal end of the second jaw member 120 to move to the right, which rotates the second jaw member 120 about the second pivot point in the opposite direction, causing the distal end of the second jaw member 120 to move away from the distal end of the first jaw member 118 (opening the end effector 108 of the instrument 100).

The arrangement of the first jaw member 118, the second jaw member 120, the first pulley 122, the second pulley 124, and the link 126 can provide a mechanical advantage for the instrument 100. For example, considering the first jaw member 118 and the first pulley 122, an input force Fin can be applied as shown in FIG. 17A by pulling on a pull wire engaged with the first pulley 122. The arrangement of the first pulley 122 and the first jaw member 118 can amplify the force to produce an output force Font as illustrated. The output force Font can be amplified such that the output force Font is greater than the input force Fin. Advantageously, the system herein provides a greater mechanical advantage than what can be achieved by a simple pulley-driven grip.

Moment arms L1, L2, L3, and L4 are illustrated in FIG. 17A. Moment arm L1 can be equal to the distance between the pulley axis 112 and the point where the force Fin is applied from the cable tension. In some embodiments, the moment arm L1 is equal to the radius of the first pulley 122 or is slightly less than the radius of the first pulley 122. The moment arm L2 can be equal to the distance 136, which as noted above is the distance between the pulley axis 112 and the first drive pin 128. In general, the moment arm L2 is less than the moment arm L1. The moment arm L3 is equal to the distance between the first drive pin 128 and the first link pin 132. In general, L3 is longer than L2. The moment arm L4 is equal to the distance between the first link pin 132 and the distal end of the first jaw member 118. A mechanical advantage can be achieved because, when the input force Fin is applied to the pull wire on the first pulley 122 at the moment arm L1 to rotate the first pulley 122 about the pulley axis 112, this moves the shorter moment arm L2 which drives the longer moment arm L3 about the first pivot (e.g., first link pin 132). Changing moment arm lengths (in particular, increasing moment arm L1 relative to moment arm L2 and/or increasing moment arm L3 relative to moment L4) can increase the mechanical advantage.

In some embodiments, to increase grip strength (e.g., output force Font), the following variables can change in the following directions: increase moment arm L1, decrease moment arm L2, increase moment arm L3, decrease moment arm L4, and/or increase the distance between pivot points (e.g., the length of the link 126). In some embodiments, the grip strength can be increased by changing the aforementioned variables in combination with a secondary geometry change. Those skilled in the art will appreciate that a wide variety of arrangements for the moment arms L1, L2, L3, and L4 are possible. Further detail about determining the mechanical advantage is described below with reference to FIGS. 26A-27. Advantageously, this arrangement (e.g., as described herein) can provide a mechanical advantage while maintaining a form factor suitable for minimally invasive surgery as described above.

As shown in the embodiment illustrated in FIGS. 17A and 17B, the first and second pulleys 122, 124 can be positioned between the proximal ends of the first and second jaw members 118, 120. However, this need not be the case in all embodiments. For example, FIGS. 18A and 18B illustrate an embodiment where the first and second jaw members 118, 120 are positioned between the first and second pulleys 122, 124. FIG. 18A illustrates this embodiment of the instrument 100 in the open position, and FIG. 18B illustrates this embodiment of the instrument 100 in the closed position.

In some embodiments, by placing the first and second pulleys 122, 124 in between the first and second jaw members 118, 120 (for example, as shown in FIGS. 17A and 17B), the first and second pulleys 122, 124 can be made with a larger diameter, which can result in a larger mechanical advantage in some instances. This can be at least in part because pulley diameter can be defined by the chord length of the circle along the plane of the pulley. As you move the pulley closer to the center of a circle, the chord length increases up to the diameter of the circle.

Figure 19A:
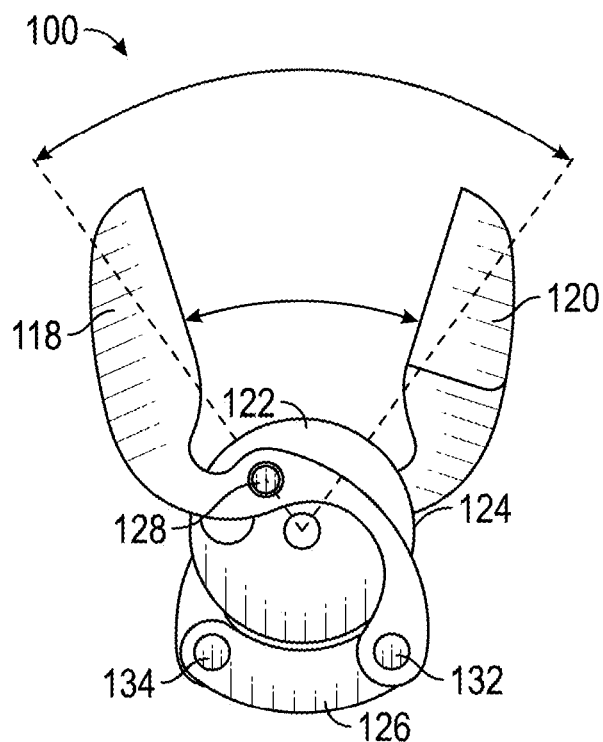
FIG. 19A illustrates another embodiment of a high force instrument in an open position.
Figure 19B:
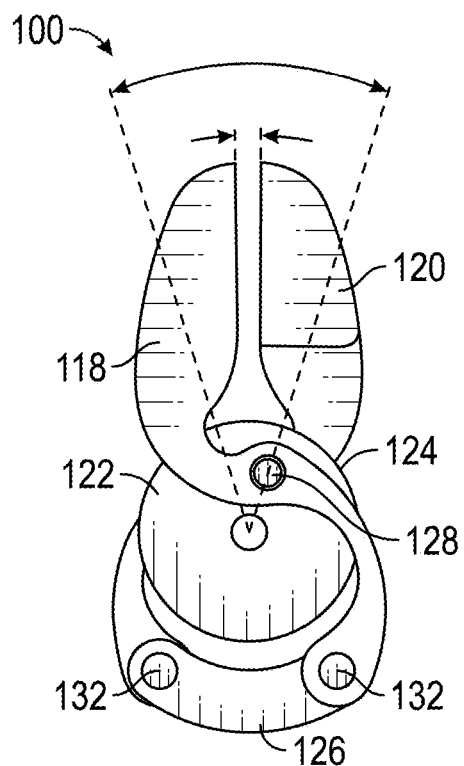
FIG. 19B illustrates the high force instrument of FIG. 19A in a closed position.

In the embodiments of the instrument 100 shown in FIGS. 17A and 17B and FIGS. 18A and 18B, the link 126 is positioned above first and second pulleys 122, 124 (relative to the illustrated orientation). This need not be the case in all embodiments. For example, FIGS. 19A and 19B illustrate an embodiment of the instrument 100 that includes the link 126 that is positioned below the first and second pulleys 122, 124. FIG. 19A illustrates this embodiment of the instrument 100 in an open position, and FIG. 19B illustrates this embodiment of the instrument 100 in a nearly closed position. Such an arrangement may be advantageous in cases where there is more room for mechanisms below the first and second pulleys 122, 124 rather than above the first and second pulleys 122, 124. In some embodiments, the instrument 100 comprises a shaft and a wrist having a large enough diameter that provides room to fit components, such as the link 126. Note that an advantage of the embodiment in FIGS. 19A and 19B is that the grips or jaw members 118, 120 are capable of opening through a smaller angle for the same open distance at the tip, thereby resulting in a more parallel closure, which can be advantageous for some instruments such as vessel sealers.

In the embodiment of the instrument 100 illustrated in FIGS. 19A and 19B, the instrument 100 can include the first jaw member 118, the second jaw member 120, the first pulley 122, the second pulley 124 (behind the first pulley 122), and the link 126 arranged as shown. In this embodiment, the first jaw member 118 is connected to the first pulley 122 by the first drive pin 128 at a position that is positioned between the proximal end of the first jaw member 118 and the distal end of the first jaw member 118. The proximal end of the first jaw member 118 is connected to the link 126 by the first link pin 132 such that the link 126 is positioned below the first pulley 122 (e.g., on the side of the first pulley 122 opposite the distal end of the first jaw member 118). Similarly, the second jaw member 120 is connected to the second pulley 124 by the second drive pin 130 (not visible) at a position that is positioned between the proximal end of the second jaw member 120 and the distal end of the second jaw member 120. The proximal end of the second jaw member 120 is connected to the link 126 by the second link pin 134 such that the link 126 is positioned below the second pulley 124 (e.g., on the side of the second pulley 124 opposite the distal end of the second jaw member 120). Like the instruments 100 shown in FIGS. 17A-18B, the instrument 100 of FIGS. 19A and 19B can also provide a mechanical advantage.

Figure 20A:
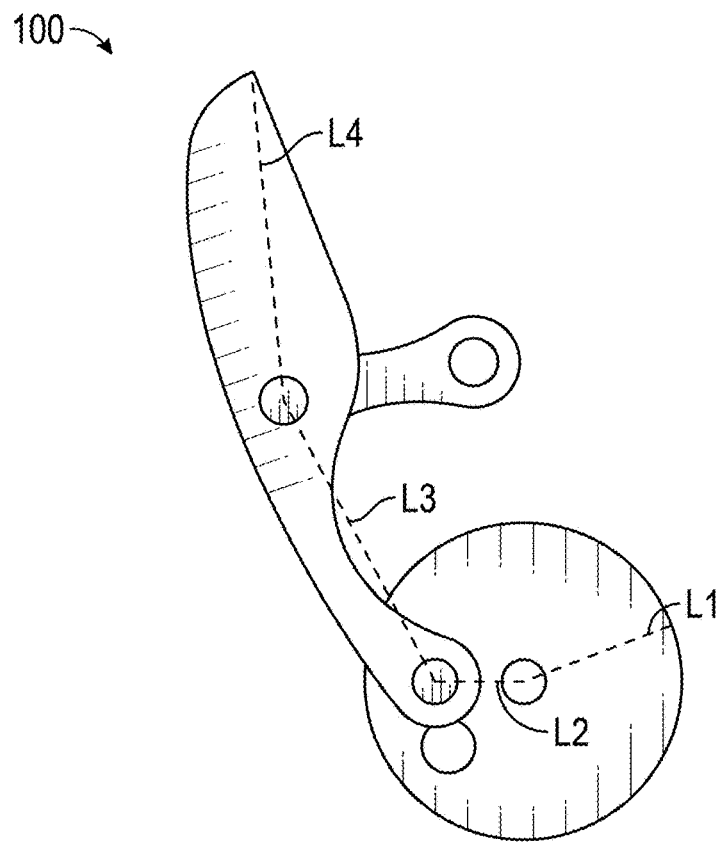
FIGS. 20A, 20B, 20C, and 20D illustrate views of components of various embodiments of high force instruments and further illustrate how the geometry can be varied to adjust a mechanical advantage of a high force instrument.
Figure 20B:
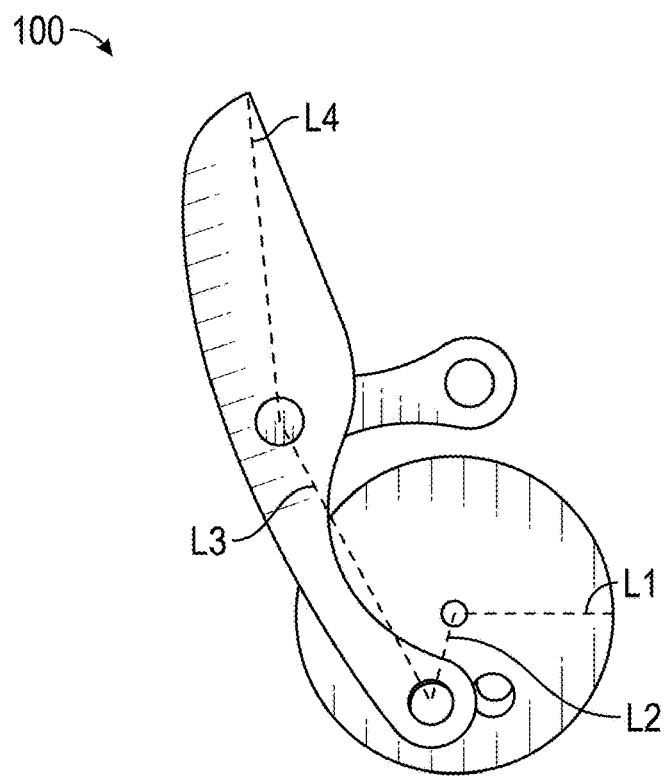
Figure 20C:
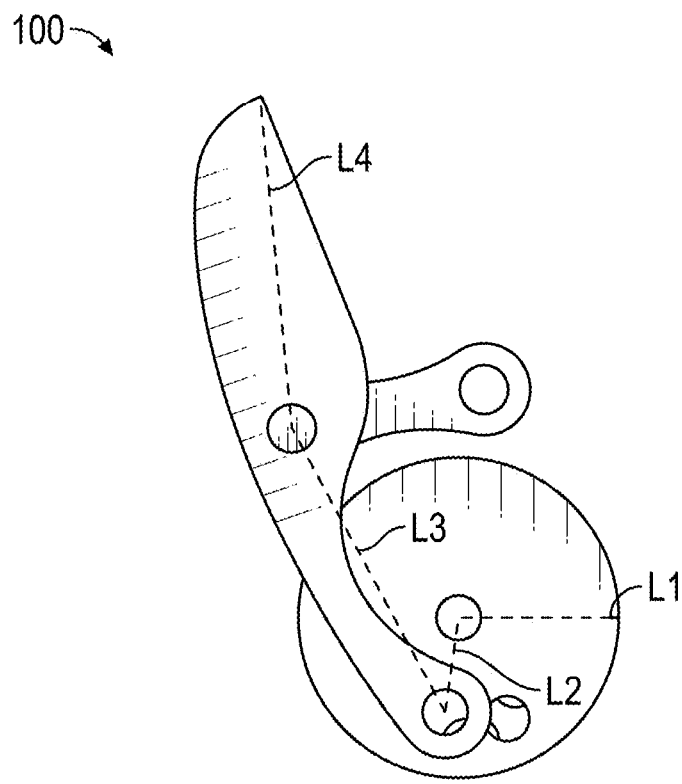
Figure 20D:
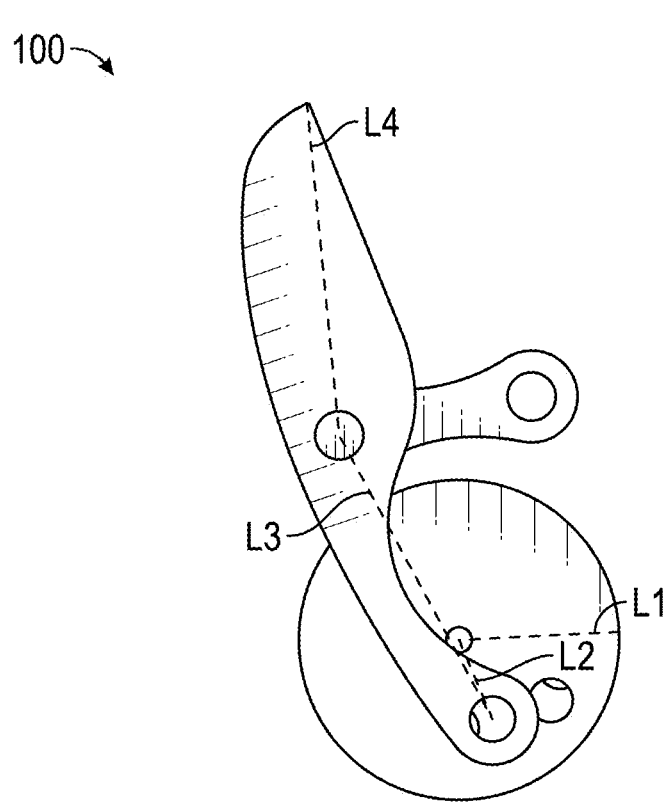

As noted above, the dimensions of the various components of the high force instruments 100 can be varied to provide different mechanical advantages. Additionally, the starting point for the pivot of L2/L3 may be adjusted to increase or decrease linear motion of the grips as they open and close, as shown in FIGS. 20A-20D. FIGS. 20A and 20B illustrate an embodiment the instrument 100 configured for high linear motion and low back drive, while FIGS. 20C and 20D illustrate an embodiment of the instrument 100 configured for low linear motion. When the L2/L3 pivot point is increased at the end, you get a mechanical leverage due to driving in a circular motion. FIGS. 20A and 20B show this at the extreme, where the two L2/L3 pivot points are directly across the diameter. In this case, any force that tries to back drive the grips is resolved through the radius of the pulley and requires no tension from the cables to maintain this point. Similarly, the mechanical leverage increases to infinity as you approach this point during closure. Accordingly, the dimensions of the components of the instrument 100 can be designed to provide an optimal trade-off of low linear motion and high mechanical advantage.

In some embodiments, first link L1 can be between 3 and 4 mm, the second distance of the second link L2 can be between 2 and 3 mm, the third distance of the third link L3 can be between 7 and 8 mm, and the fourth distance of the fourth link L4 can be between 17 and 23 mm. For example, in one embodiment, the first distance of the first link L1 is approximately 3.35 mm, the second distance of the second link L2 is approximately 2.5 mm, the third distance of the third link L3 is approximately 7.3 mm, and the fourth distance of the fourth link L4 is approximately 20 mm. In some embodiments, a first ratio between the second distance of the second link L2 and the first distance of the first link L1 is between 0.5 and 1.25, a second ratio between the third distance of the third link L3 and the first distance of the first link L1 is between 1.5 and 3.5, and a third ratio between the fourth distance of the fourth link L4 and the first distance of the first link L1 is between 1.5 and 20. For example, in one embodiment, the first ratio between the second distance of the second link L2 and the first distance of the first link L1 is approximately 0.75, the second ratio between the third distance of the third link L3 and the first distance of the first link L1 is approximately 2.18, and a third ratio between the fourth distance of the fourth link L4 and the first distance of the first link L1 is approximately 6. Other sizes for the links L1, L2, L3, and L4, as well as other ratios between the links are also possible.

Figure 21:
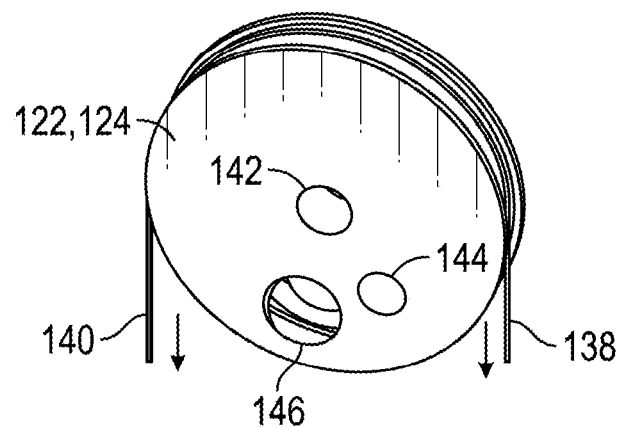
FIG. 21 illustrates a perspective view of an embodiment of a pulley wrapped with a pull wire.

FIG. 21 illustrates an example of a pulley (e.g., the first pulley 122 or the second pulley 124) engaged with two cable or pull wires 138, 140 engaged with the pulley in an a-wrap configuration. In some embodiments, the pull wires 138, 140 are actually cable or pull wire segments 138, 140 that are part of a single cable or wire separated by a medial crimp. As illustrated, in the a-wrap configuration, the first pull wire 138 extends over a first side of the pulley (e.g., the right side in the figure), over the top of the pulley, and down a second side of the pulley (e.g., the left side in the figure), before terminating in a crimp pocket 146. Within the crimp pocket 146 the end of the first pull wire 138 is connected or otherwise fixed to the pulley via the medial crimp. Because the first pull wire 138 wraps nearly all the way around the pulley before terminating at the crimp pocket 146, this provides that a large amount of rotation can be accomplished by pulling the pull wire 138. For example, the pull wire 138 can cause the pulley to rotate in the clockwise direction from the position illustrated all the way around until where the crimp pocket 146 is positioned at the first side of the pulley. In some embodiments, this can allow, for example, about or greater than 270 degrees of rotation.

The second pull wire 140 is similarly wrapped around the pulley, but in the opposite direction. As illustrated, the second pull wire 140 extends over the second side of the pulley (e.g., the left side in the figure), over the top of the pulley, and down the first side of the pulley (e.g., the ride side in the figure), before terminating at the crimp pocket 146. Thus, the second pull wire 140 can similarly allow a large rotation of the pulley (e.g., about or greater than 270 degrees) in the counterclockwise direction.

In some embodiments, the first pull wire 138 and the second pull wire 140 are a single pull wire wrapped continuously around the pulley and fixed to the pulley in the crimp pocket 146.

An a-wrap configuration as shown in FIG. 21 can be advantageous in the high force instruments 100 described herein because the mechanical advantage of these instruments 100 converts larger pulley rotations into higher forces. Accordingly, the pulley can be configured to allow for larger rotations, which can in some instances accommodate a larger range of motion of the instrument.

FIG. 21 also illustrates that the pulley 122, 124 can include a bore 142 configured to receive a pin about which the pulley rotates, and a drive pin bore 144 configured to receive the drive pins 128, 130.

In some embodiments, high force instruments 100 can include one or more constraints. As will be described below, the constraints can help to ensure that motion of the high force instrument 100 (e.g., opening and closing the first and second jaw members 118, 120) is consistent and accurate and/or to stabilize the instrument 100. In certain instances, some embodiments of high force instruments 100 may exhibit unwanted parallelogram motion unless an additional constraint is incorporated into the design. For example, in some embodiments, without a constraint, the first and second jaw members 118, 120 can shift relative to each other (e.g., the first jaw member 118 can shift in an upward direction and the second jaw member 120 can shift in a downward direction) rather than opening and closing as desired. In some embodiments, this undesirable motion is caused by having a multi-link system (e.g., four links) with two pivot points. Inclusion of one or more constraints can eliminate, help prevent, or reduce this undesirable motion, thereby stabilizing the high force instrument 100. For example, an additional constraint can be incorporated that keeps the first and second jaw members 118, 120 from sliding relative to each other. Various types of constraints are possible and are described in further detail below.

Figure 22A:
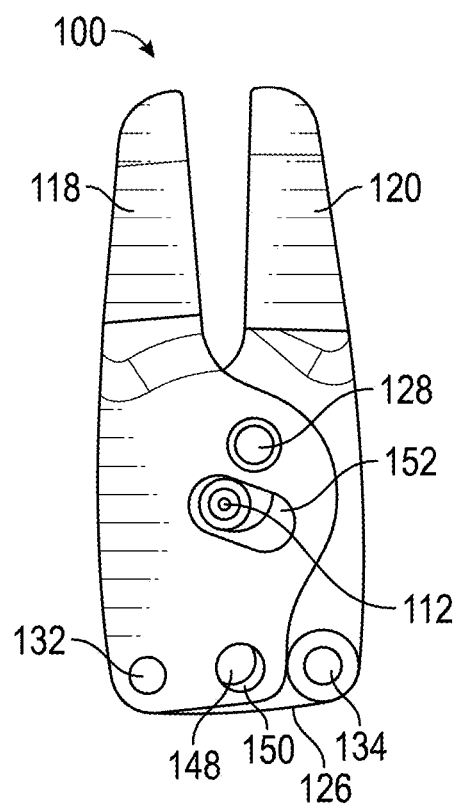
FIGS. 22A, 22B, and 22C illustrate views of an embodiment of a high force instrument that includes a geared constraint configured as a pin based cycloid constraint.
Figure 22B:
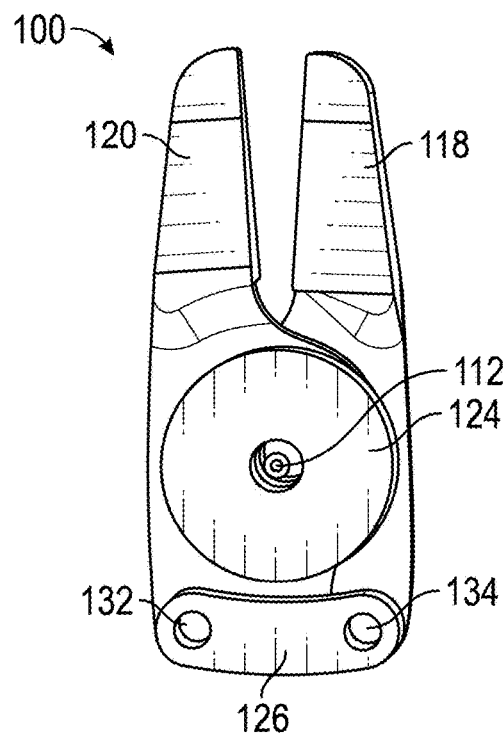
Figure 22C:
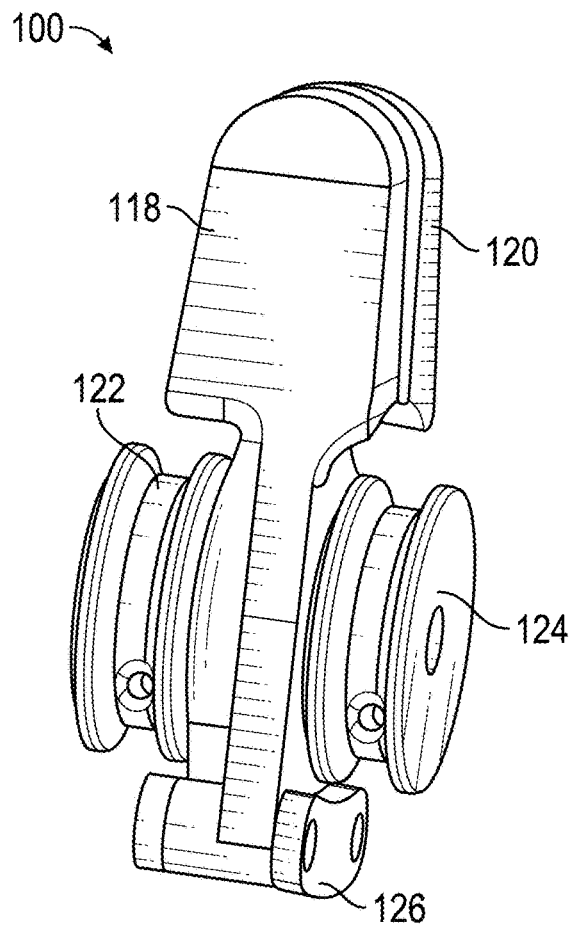

FIGS. 22A-22C illustrate views of an embodiment of the high force instrument 100 that includes a constraint formed by a constraint pin 148 and a constraint slot 150. FIG. 22A illustrates a front view of this embodiment of the high force instrument 100, FIG. 22B illustrates a back view of this embodiment of the high force instrument 100, and FIG. 22C illustrates a side perspective view of this embodiment of the high force instrument 100. Note that in FIG. 22A, the pulley 124 and part of the constraint bar or link 126 are hidden from view. The instrument 100 of FIGS. 22A-22C includes the first jaw member 118, the second jaw member 120, the first pulley 122, the second pulley 124, and the link 126 arranged as shown. In the illustrated embodiment, the link 126 is positioned below the first and second pulleys 122, 124. The first jaw member 118 is connected to the first pulley 122 by the first drive pin 128. The second jaw member 120 is connected to the second pulley 124 by the second drive pin 130. The first and second pulleys 122, 124 rotate around the pulley axis 112.

As illustrated, the instrument 100 additionally includes a constraint pin 148 and a constraint slot 150. The constraint pin 148 is formed on (or connected to) one of the grip or jaw members (e.g., 120) and extends through a constraint slot 150 formed in the other grip or jaw member (e.g., 118), thereby providing a geared motion between jaw members 118, 120. As shown, the first jaw member 118 is connected to the link 126 by the first link pin 132. The constraint slot 150 can be formed as a curve or cycloid (e.g., formed at a constant radius). In some embodiments, a cycloid curve is formed by the path traced by constraint pin 148 in the grip or jaw member 118 as the jaw members 118, 120 are opened or closed through a range of motion, thereby maintaining symmetric angles between the jaw members and midplane. When such a cycloid curve is formed, you advantageously constrain the motion of the jaw members 118, 120. In other words, the cycloid curve can match the path of the constraint pin 148 when the first and second jaw members 118, 120 are moved symmetrically to open and close. The constraint pin 148 and constraint slot 150 can keep the first and second jaw members 118, 120 from shifting in a parallel motion, thereby maintaining a symmetric angle about the midplane. For example, this can allow the constraint pin 148 to move through the constraint slot 150 as the first jaw member 118 pivots about the first link pin 132. That is, the constraint slot 150 can provide an additional connection between the first jaw member 118 and the second jaw member 120, while still allowing the first jaw member 118 to pivot relative to the link 126 about the first link pin 132. In some embodiment, this may help prevent the undesirable shifting described above and can stabilize the motion of the instrument 100.

While in the present embodiment, the constraint pin 148 extends from the jaw member 120 and into a constraint slot 150 formed in the jaw member 118, in other embodiments, the constraint pin 148 extends from the jaw member 118 and into a constraint slot 150 formed in the jaw member 120.

Additionally, for some embodiments, the constraint pin 148 and the constraint slot 150 can constrain motion of the first jaw member 118 to motion of the second jaw member 120. That is, these constraints can cause motion of the first jaw member 118 to cause a corresponding motion of the second jaw member 120 (or vice versa). For example, if the first jaw member 118 opens five degrees, these constraints cause the second jaw member 120 to open five degrees. In some embodiments, the corresponding motion of the second jaw member 120 is imperfect such that it will not correspond exactly to motion of the first jaw member 118 (e.g., if the first jaw member 118 opens five degrees, these constraints can cause the second jaw member 120 to open 5.5 degrees).

In some embodiments, these constraints (e.g., the constraint pin 148 and the constraint slot 150) can be considered a pin based cycloid constraint. In some embodiments, these constraints can be considered a geared restraint because they gear motion of the first jaw member 118 to motion of the second jaw member 120.

FIG. 22A also illustrates that, in some embodiments, the instrument 100 can include a pulley axle clearance slot 152. The pulley axle clearance slot 152 can help to provide clearance for the motion of the first jaw member 118 over the pulley drive pin, so that the first jaw member 118 will open and not be limited in its range of motion. Although not visible, the second jaw member 120 can also include a similar pulley axle clearance slot.

Figure 23:
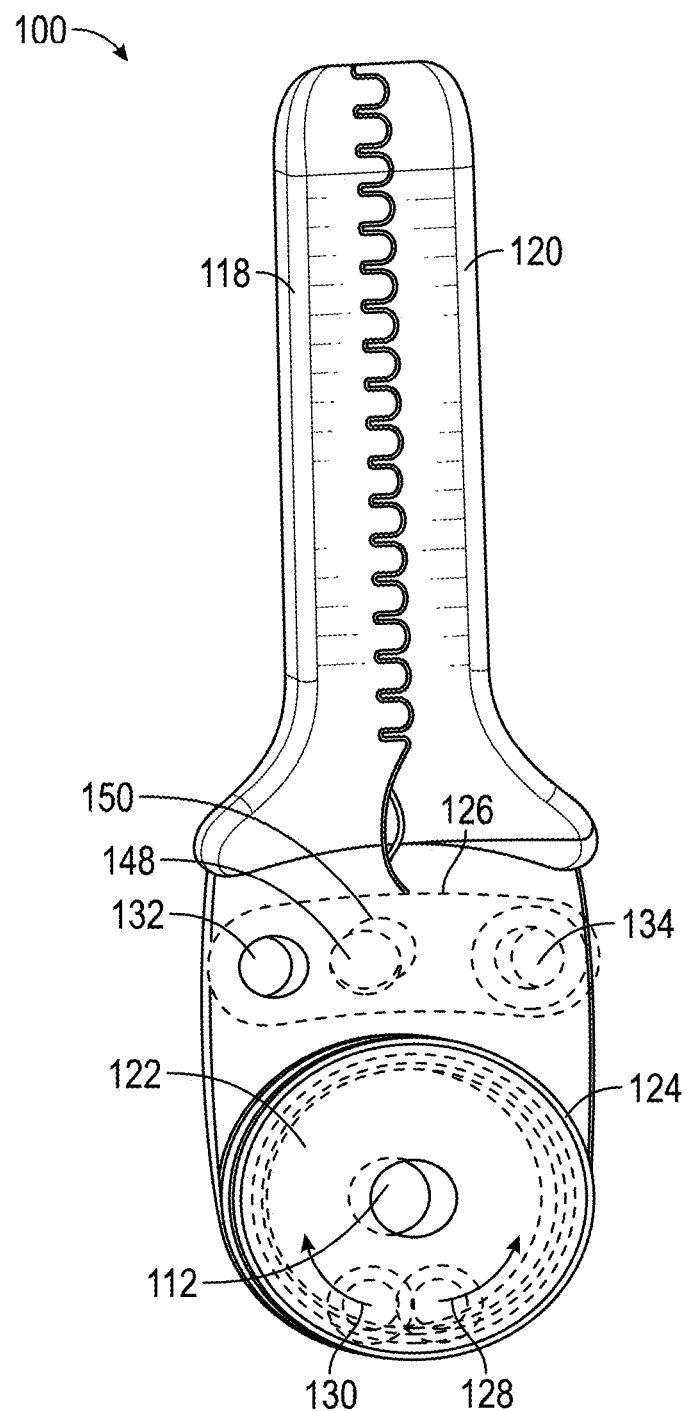
FIG. 23 illustrates a view of another embodiment of a high force instrument that includes a geared constraint configured as a pin based cycloid constraint.

FIG. 23 illustrates a front view of another embodiment of the high force instrument 100 that includes the constraint pin 148 and the constraint slot 150 (similar to those described above), and which is further configured such that the drive pins 128, 130 are positioned so that they never move to a position where they overlap. In some embodiments, it has been observed that if the drive pins 128, 130 move to a position in which they overlap, the first and second jaw members 118, 120 can rotate or pivot together around the aligned drive pins 128, 130. Keeping the drive pins 128, 130 apart, either in a radial distance, an angular distance, or both, may help to prevent this motion.

The instrument 100 of FIG. 23 includes the first jaw member 118, the second jaw member 120, the first pulley 122, the second pulley 124, and the link 126 arranged as shown. In the illustrated embodiment, the link 126 is positioned above the first and second pulleys 122, 124. The first jaw member 118 is connected to the first pulley 122 by the first drive pin 128, and the second jaw member 120 is connected to the second pulley 124 by the second drive pin 130. The first and second pulleys 122, 124 rotate around the pulley axis 112 as described above. Additionally, the instrument 100 includes the constraint pin 148 and the constraint slot 150 as described above. Although in this embodiment, the link 126 is positioned above the pulleys 122, 124.

In addition, in this embodiment, each of the drive pins 128, 130 are positioned so that they never move to an overlapping position. For example, the instrument 100 is illustrated in a closed position (with the first jaw member 118 contacting the second jaw member 120), and in this position, the drive pins 128, 130 are positioned as shown. Because the first jaw member 118 contacts the second jaw member 120, the first drive pin 128 is prevented from further rotation in the clockwise direction and the second drive pin 130 is prevented from further rotation in the counterclockwise direction. From this position, the first and second drive pins 128, 130 can only rotate in the directions indicated with arrows in the figure. That is, as the instrument 100 opens, the first drive pin 128 can only rotate in the counterclockwise direction and the second drive pin 130 can only rotate in the clockwise direction. As such, the first and second drive pins 128, 130 are positioned so as to not overlap during any portion of the motion, which can improve the stability of the instrument 100.

In some embodiments, by keeping the drive pins 128, 130 apart (e.g., preventing overlapping), the range of motion of the first and second jaw members 118, 120 can be limited. This is because preventing the drive pins 128, 130 from overlapping reduces the total amount of rotation available for each of the first and second pulleys 122, 124. This can reduce the total amount of work (and thus force) that can be transferred from the input to the output. Thus, some embodiments that include non-overlapping drive pins 128, 130 (like the instrument 100 of FIG. 23) trade jaw motion or force amplification for stability. Those of skill in the art will, upon consideration of this disclosure, appreciate that this trade off can be selected so at to maximize performance of the instrument 100 for a given situation.

In some embodiments, even with a pin based cycloid constraint (such as the constraint formed by the constraint pin 148 and the constraint slot 150 in FIGS. 22A and 23), the instrument 100 may still exhibit undesirable instability due to manufacturing tolerance stack up. In some embodiments, this instability can be eliminated or reduced, by replacing the pin based cycloid constraint with a tooth based cycloid constraint. Like a pin based cycloid constraint, a tooth based cycloid constraint can be considered a type of geared constraint. With a tooth based cycloid constraint, one jaw member is formed with a tooth that extends into a notch of the other jaw member, thereby helping to prevent undesirable shifting of the jaw members during use. The embodiments of the instrument 100 shown in FIGS. 24A-24H and FIGS. 25A-25H described below, include examples of a tooth based cycloid constraint.

In some embodiments, to address the drawbacks associated with preventing the drive pins 128, 130 from overlapping, rather than limiting the ability of the drive pins 128, 130 to overlap and cross, the instrument 100 can include a slot constraint. The slot constraint can prevent or reduce instability in the instrument 100 even while the drive pins 128, 130 overlap. As will be described in greater detail below, the slot constraint can be formed as a trough or slot between two ears. As the drive pins 128, 130 overlap into alignment and cross over, the ears of the slot constraint can abut and contact the central pin of the pulleys 122, 124, thereby preventing undesirable rotation of the first and second jaw members 118, 120. As the drive pins are capable of crossing, these designs may include a unique feature in that they are capable of getting more force advantage than designs that limit or prevent crossing of the drive pins 128, 130. In addition, these designs can provide a unique force profile in which the gripping force is highest when the grips are closed (see FIG. 27 below and the corresponding description). FIGS. 24A-24H illustrate an embodiment that includes a slot constraint.

Figure 24A:
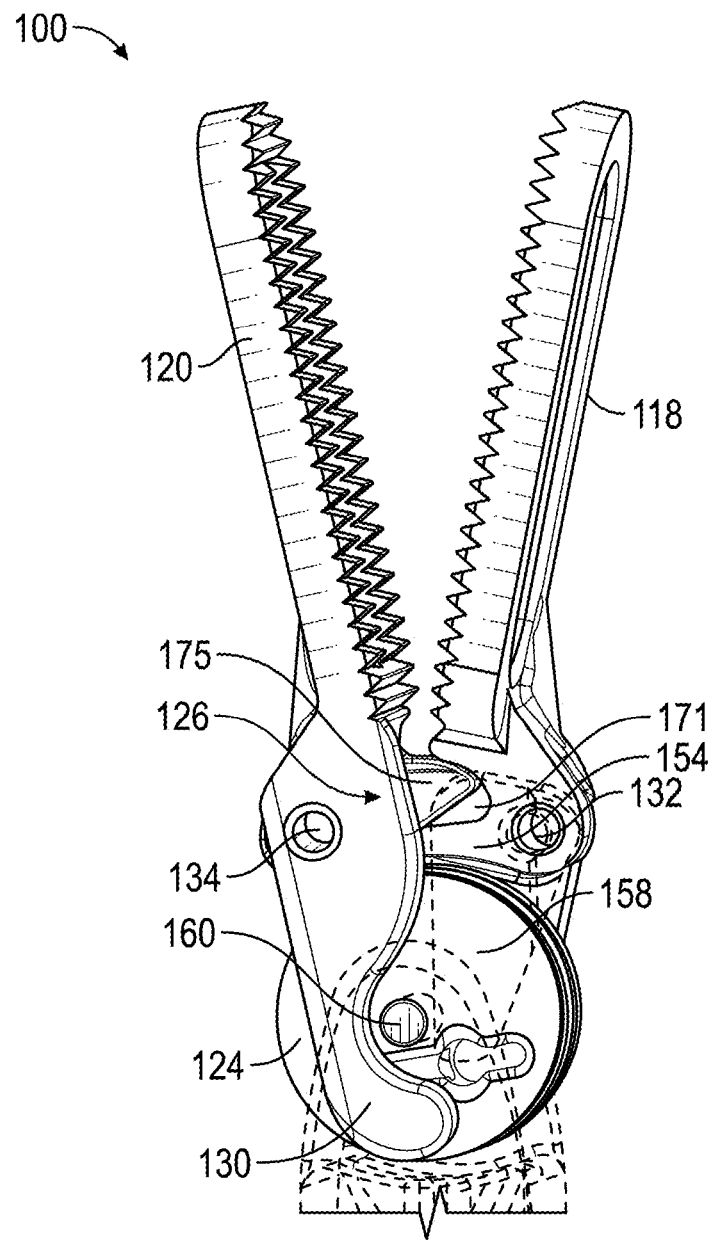
Figure 24B:
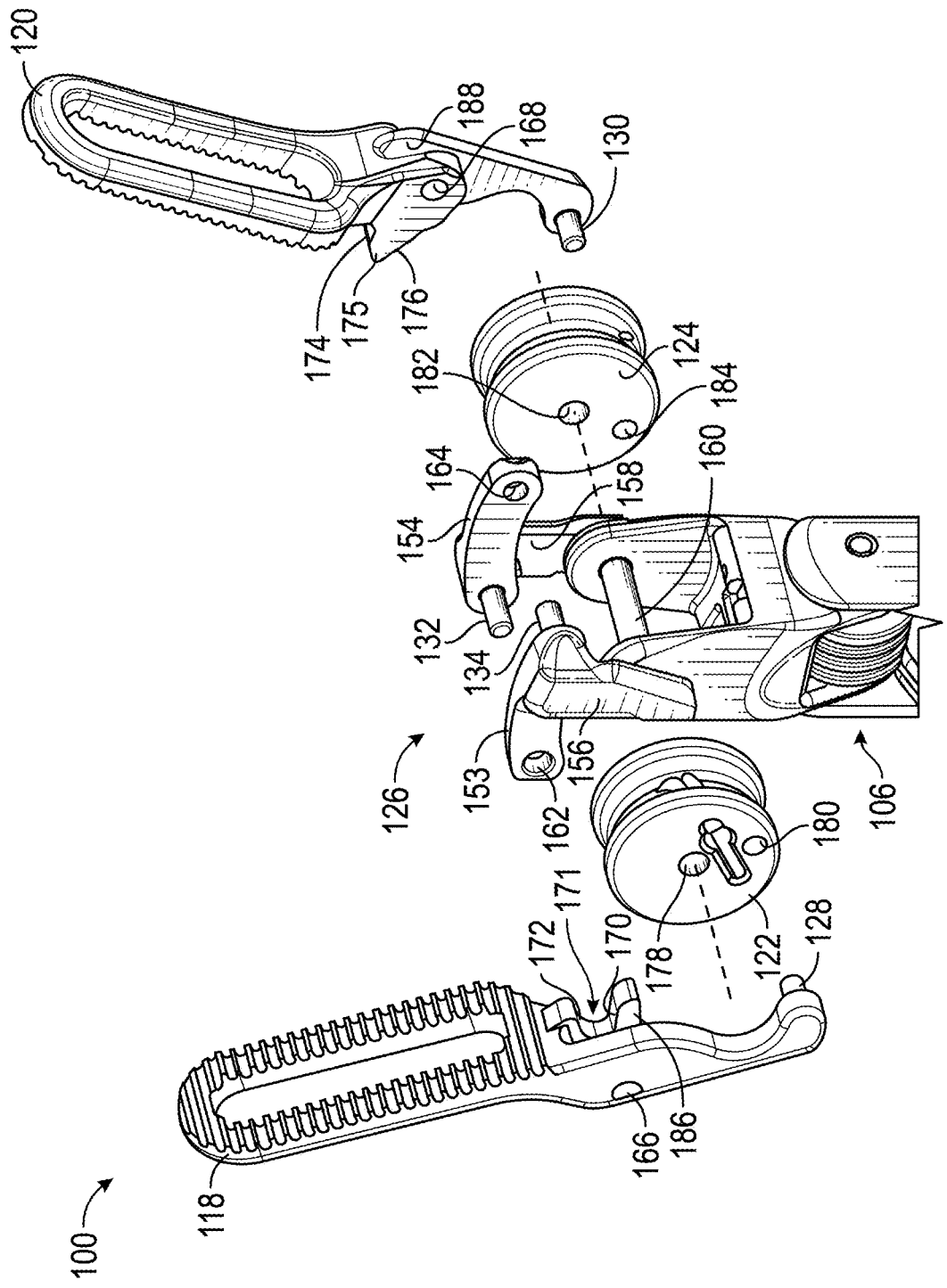
Figure 24C:
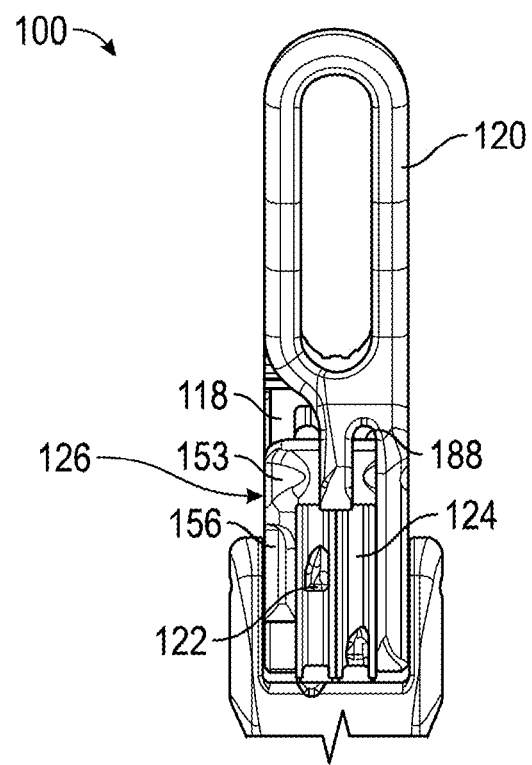
Figure 24D:
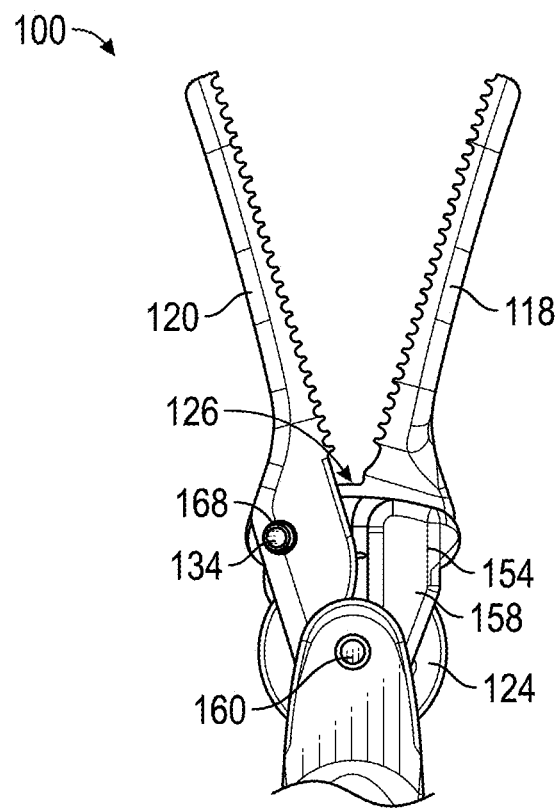
Figure 24E:
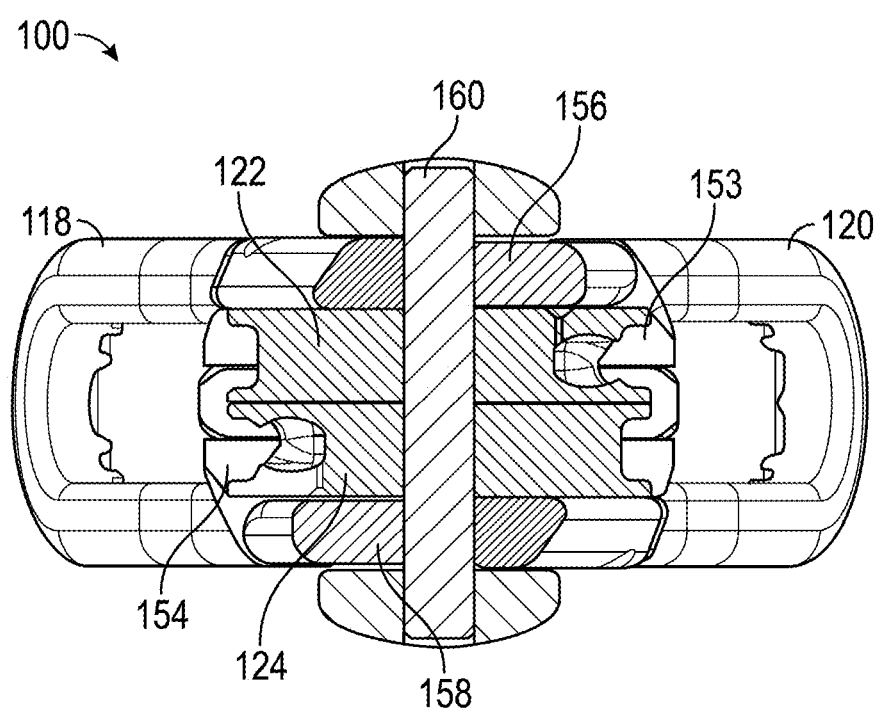

FIGS. 24A-24H illustrate views of an embodiment of the high force instrument 100 that includes a geared constraint (configured as a tooth based cycloid constraint) and a slot constraint. FIG. 24A is a front view of the instrument 100 in an open position, FIG. 24B is an exploded view of the instrument 100, FIG. 24C is a side view of the instrument 100, FIG. 24D is a back view of the instrument 100 in an open position, and FIG. 24E is a bottom cross-sectional view of the instrument 100 through the center pin. FIGS. 24F-24H illustrate the drive pins 128, 130 crossing as the instrument 100 moves from an open position to a closed position.

As best shown in the exploded view of FIG. 24B, the instrument 100 includes the first jaw member 118, which can be configured as shown. For example, the first jaw member 118 can include the first drive pin 128 positioned at the proximal end of the first jaw member 118. Alternatively, the first drive pin 128 may be formed as part of the first pulley 122 or as a separate piece as mentioned above. The first jaw member 118 may also include a hole or opening 166, which provides line of site access to the junction of first link pin 132 and opening 162 (discussed below), so that the assembly can be laser welded together if desired. An additional hole, opening, recess or divot (not shown) can be formed on an inner surface of the first jaw member 118 to engage the pin 132. The first jaw member 118 may also include a notch 171 formed by an upper surface 172 and a lower surface 170. As will be described below, the upper and lower surfaces 172, 170 that form the first notch will engage with corresponding features on the second jaw member 120 to form a geared constraint or tooth based cycloid constraint (see FIG. 24A, for example). The first jaw member 118 may also include a slot 186. The slot 186 may be configured to receive an end of a first piece 153 of the link 126.

The second jaw member 120 can include the second drive pin 130 positioned at the proximal end of the second jaw member 120. Alternatively, the second drive pin 130 may be formed as part of the second pulley 124 or as a separate piece as mentioned above. The second jaw member 120 may also include an opening 168 configured to receive the second link pin 134. The second jaw member 120 may also include a tooth 175 having an upper surface 174 and a lower surface 176. As will be described below, the upper and lower surfaces 174, 176 of the tooth 174 will engage with corresponding features on the first jaw member 118 to form the geared constraint or tooth based cycloid constraint (see FIG. 24A, for example). The second jaw member 120 may also include a slot 188. The slot 188 may be configured to receive an end of a second piece 154 of the link 126. In some embodiments, the tooth 175 comprises an extension or protrusion that can appear as a triangular fin. In other embodiments, the tooth 175 comprises an extension or protrusion in another shape, such as peg-shaped. The recess or notch 171 that receives the tooth 175 is large enough to provide clearance for the tooth 175 as the jaw members 118, 120 open and close. In some embodiments, a cycloid constraint is formed such that the lower surface 170 of the notch 171 is maintained in contact with the lower surface 174 of the tooth 175, while the upper surface of the notch 172 is maintained in contact with the upper surface 176 of the tooth 175 during the opening and closing of the jaw members.

The first pulley 122 may include a pulley axis opening 178. The pulley axis opening is configured to be mounted on a pulley pin 160. The pulley pin 160 may be aligned with the pulley axis 112 (described above). The first pulley 122 rotates about the pulley pin 160. The first pulley 122 may also include a hole 180 for receiving the first drive pin 128. Similarly, the second pulley 124 may include a pulley axis opening 182 configured to be mounted on the pulley pin 160 to allow the second pulley 124 to rotate about the pulley pin 160. The second pulley 124 may also include a hole 184 for receiving the second drive pin 130.

In the embodiment of FIGS. 24A-24H, the link 126 is formed by a first piece 153 and a second piece 154. The first piece 153 includes an opening 162 for receiving the first link pin 132 therethrough. The portion of the first piece 153 that includes the opening 162 may be configured so as to be received in the slot 186 of the first jaw member 118, such that the first link pin 132 can extend through the opening 162 in the first piece and into or through the opening 166 in the first jaw member 118. As shown in FIG. 24B, the first piece 153 of the link 126 may also include the second link pin 134. In some embodiments, the second link pin 134 is integrally formed with the first piece 153. In other embodiments, the second link pin 134 can be a separate piece or integrally formed with the second jaw member 120. The first piece 153 of the link 126 also includes an ear 156 as shown. The ear 156 can be formed as a downward projection or protrusion. As will be discussed below, an inner surface of the ear 156 can contact the pulley pin 160 when assembled to prevent or reduce instability in the instrument 100 when the drive pins 128, 130 are aligned.

As mentioned above, the link 126 can be formed by the first piece 153 and the second piece 154. The second piece 154 can include an opening 164 for receiving the second link pin 134 therethrough. The portion of the second piece 154 that includes the opening 164 may be configured so as to be received in the slot 188 of the second jaw member 120, such that the second link pin 134 can extend through the opening 164 in the second piece 154 and into or through the opening 168 in the second jaw member 120. As shown in FIG. 24B, the second piece 154 of the link 126 may also include the first link pin 132. In some embodiments, the first link pin 132 is integrally formed with the second piece 154. In other embodiments, the first link pin 132 can be a separate piece or integrally formed with the first jaw member 118. The second piece 154 of the link 126 also includes an ear 158 as shown. The ear 158 can be formed as a downward projection or protrusion. As will be discussed below, an inner surface of the ear 158 can contact the pulley pin 160 when assembled to prevent or reduce instability in the instrument 100 when the drive pins 128, 130 are aligned.

As shown for example in FIG. 24A, when assembled, the tooth 175 of the second jaw member 120 is received in the groove or notch 171 of the first jaw member 118. This interaction between the first and second jaw members 118, 120 provides a geared restraint or a tooth based cycloid restraint for the instrument 100. This constraint can constrain motion of the first jaw member 118 to the second jaw member 120 similar to the pin based cycloid restraint described above with reference to FIGS. 22A and 23. This constraint can also improve the stability of the instrument 100 by, for example, preventing or reducing parallel motion between the first and second jaw members 118, 120. In some embodiments, an advantage of this constraint is that it may be less susceptible to manufacturing tolerance errors than other types of restraints, such as the pin based cycloid constraint. In other embodiments, more than one tooth (e.g., first and second teeth) can be provided between the first and second jaw members to provide a tooth-based geared constraint.

Additionally, when assembled, the instrument 100 can include a slot constraint that is configured to prevent instability when the drive pins 128, 130 are aligned. This can mean that the embodiment of FIGS. 24A-24H can advantageously be used in designs that allow the drive pins 128, 130 to overlap or cross. By having the drive pins 128, 130 overlap or cross, more work can be performed by the pulleys, thereby resulting in a desirable greater force output. As shown in FIGS. 24A, 24D, and 24E, the pulley pin 160 is received between the first jaw member 118 and the ear 156 of the first piece 153 of the link 126. Similarly, the pulley pin 160 is also received between the second jaw member 120 and the ear 158 of the second piece 154 of the link 126. In some embodiments, the ears 156, 158 of the first and second pieces 153, 154 of the link 126 form a slot or channel. The pulley pin 160 rides within and contacts this channel during motion of the instrument 100. This contact provides an added point of stability, which can stabilize the instrument 100 while the drive pins 128, 130 overlap.

FIGS. 24F-24H illustrate the function of the slot restraint (formed by the ears 156, 158 and the pulley pin 160) to stabilize the instrument 100 while the drive pins 128, 130 overlap and cross during motion of the instrument 100. FIGS. 24F-24H illustrate various stages during a closing motion of the instrument 100. As shown in FIG. 24F, the first and second jaw members 118, 120 are in an open position and the first drive pin 128 is located to the right (relative to the orientation shown in the figure) of the second drive pin 130. The instrument 100 is in a relatively stable position because the drive pins 128, 130 are spaced apart. This position is further stabilized by the additional contact of the pulley pin 160 with the slot formed between the ears 156, 158.

As the instrument 100 closes further, to the position illustrated in FIG. 24G, the drive pins 128, 130 begin to overlap and cross. Specifically, the first drive pin 128 has rotated clockwise from the position in FIG. 24F to the position shown in FIG. 24G, and the second drive pin 130 has rotated counterclockwise from the position in FIG. 24F to the position shown in FIG. 24G. In this position (FIG. 24G), with the drive pins 128, 130 overlapping as shown, the instrument 100 would be in a relatively unstable position absent the slot constraint formed by the pulley pin 160 and the ears 158, 156. That is, absent the slot constraint, the instrument 100 may tend to rotate about the axis of the aligned drive pins 128, 130. The slot constraint, however, advantageously stabilizes the instrument 100 against this motion. For example, contact between the pulley pin 160 and the ear 156 prevents the instrument from rotating in a clockwise direction and contact between the pulley pin 160 and the ear 158 prevents the instrument from rotating in a counterclockwise direction.

As shown in FIG. 24H, as the instrument 100 closes further, the drive pins 128, 130 rotate pass each other. For example, the first drive pin 128 is now positioned to the left of the second drive pin 130. Again, this position is relatively stable because the drive pins 128, 130 are separated and the slot constraint provides additional stability.

Considering the position of the pulley pin 160 with the slot formed between the ears 156, 158 in FIGS. 24F-24H, it can be seen that, in some embodiments, the pulley pin 160 moves along the slot during motion of the instrument 100.

The embodiment of the instrument 100 shown in FIGS. 24A-24H expands upon the force amplification and constraint concepts described above with reference to the previous embodiments by including both the geared restraint (e.g., the tooth based cycloid constraint) and the slot constraint. In some circumstances, both the constraints may have limits to their pulley range of motion, but, advantageously, such limits can occur at different angles. The two constraints can be implemented together, and thus it is possible to have an instrument that includes both constraints (as shown in FIGS. 24A-24H). By using both constraints, it is possible to extend the range of motion of the pulleys 122, 124 to be almost double that of an embodiment that limits crossing of the drive pins. This in turn increases the amount of force that can be delivered for a given range of motion. Having both constraints can reduce the instability to be approximately the minimum of either constraint at either angle.

Figure 25B:
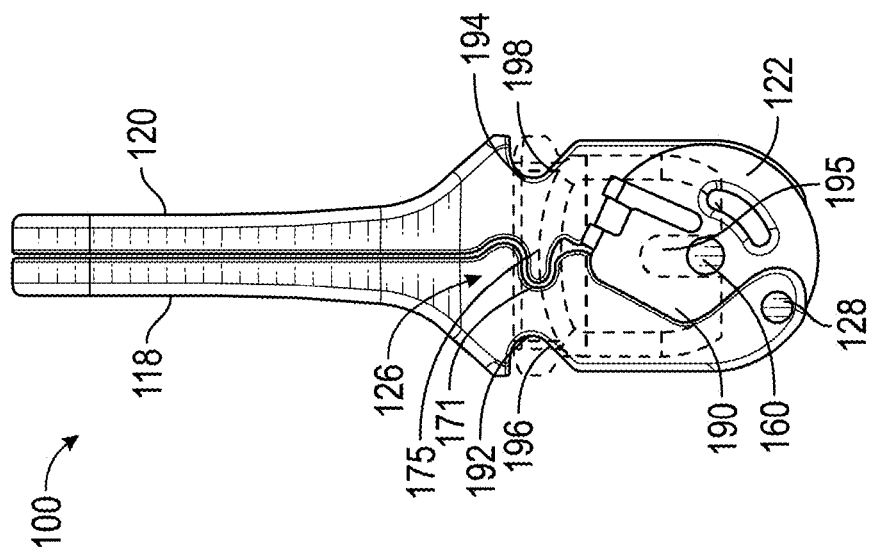
FIGS. 25A-25H illustrate views of an embodiment of a high force instrument that includes two constraints and a single piece link.
Figure 25A:
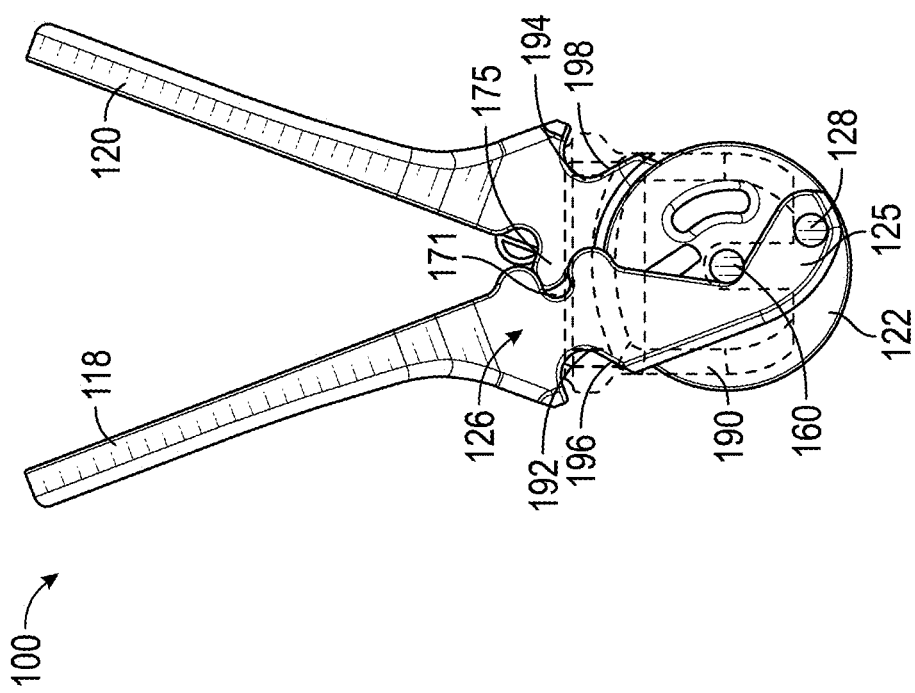
Figure 25C:
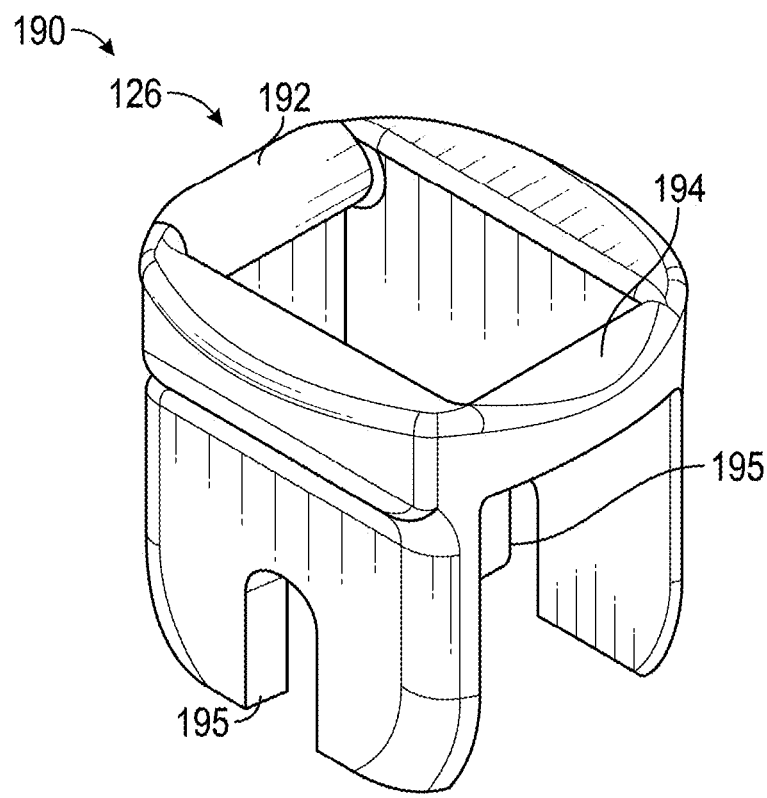
Figure 25D:
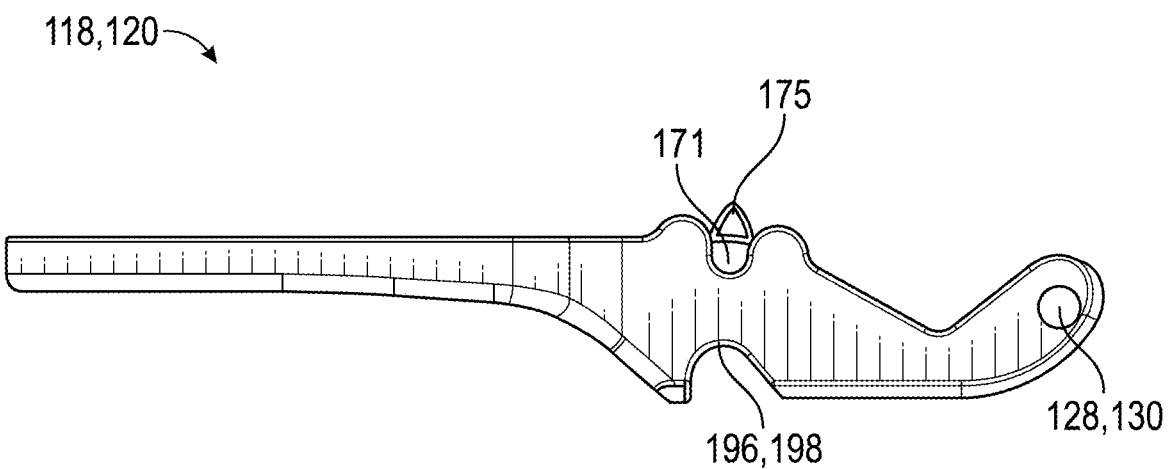

FIGS. 25A-25H illustrate an embodiment of the instrument 100 that includes two constraints as described above, but that reduces the overall number of components in the instrument 100. Such an embodiment may advantageously simplify manufacture and assembly of the instrument 100. FIGS. 25A and 25B illustrate views of the instrument 100 in an open and closed configuration, respectively. FIG. 25C illustrates an embodiment of a housing 190 that serves as the link 126 for the instrument 100. FIG. 25D illustrates a view of the first or second jaw member 118, 120. FIGS. 25E-25H illustrate stages during an example assembly process for the instrument 100.

As shown in FIGS. 25A and 25B, and shown alone in FIG. 25C, the instrument 100 includes a link 126 that is formed as a single housing 190. As best seen in FIG. 25C, the housing 190 can include a first bearing surface 192 and a second bearing surface 194. Each of the first and second bearing surfaces 192, 194 can be formed as a rod or cylinder extending across the housing 190. As will be described below, the bearing surfaces 192, 194 provide the pivot points on which the first and second jaw members 118, 120 can pivot. In some respects, the first and second bearing surfaces replace the first and second link pins 132, 134 in the previously described embodiments.

The housing 190 can also include a slot 195 as shown. The slot 195 can be configured to engage the pulley pin 160 to form the slot constraint described above. The slot constraint can provide stability for the instrument 100 when the drive pins 128, 130 are aligned.

In some embodiments, the housing 190 advantageously provides the same functionality as the first and second pieces 153, 154 of the link 126 of the embodiment of FIGS. 24A-24H in only a single piece. This may advantageously reduce the complexity of the design.

FIG. 25D illustrates an embodiment a jaw member (either the first jaw member 118 or the second jaw member 120). In FIG. 25D, the described features have been numbered twice to describe both the first jaw member 118 and the second jaw member 120. As illustrated, the jaw member 118, 120 includes a tooth 175 configured to engage a corresponding recess 171 on the opposite jaw member. The interactions between the teeth 175 and the recesses 171 provide a geared restraint (or a tooth based cycloid constraint) as described above.

The jaw members 118, 120 also include a groove 196, 198. The grooves 196, 198 are configured to receive the bearing surfaces 192, 194 of the housing 190. For example, when assembled (FIGS. 25A and 25B) the groove 196 of the first jaw member 118 receives the first bearing surface 192 to allow the first jaw member 118 to pivot about the first bearing surface 192. Similarly, the groove 198 of the second jaw member 120 receives the second bearing surface 194 to allow the second jaw member 120 to pivot about the second bearing surface 194.

As shown in FIGS. 25A and 25B, the teeth 175 and the recesses 171 provide the geared restraint (or a tooth based cycloid constraint) and the slot 195 and pulley pin 160 provide the slot restraint. Accordingly, the embodiment of the instrument 100 of FIGS. 25A-25H can provide the same advantages as the embodiment of the instrument 100 of FIGS. 24A-24H described above. Additionally, the total number of parts of the embodiment of the instrument 100 of FIGS. 25A-25H is reduced.

Figure 25E:
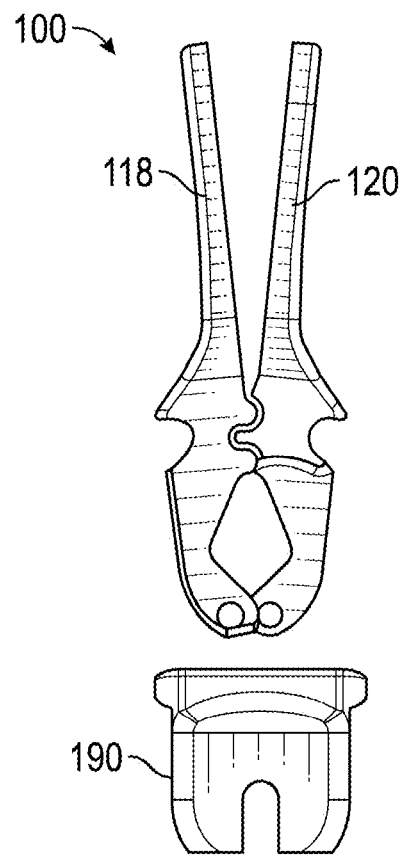
Figure 25F:
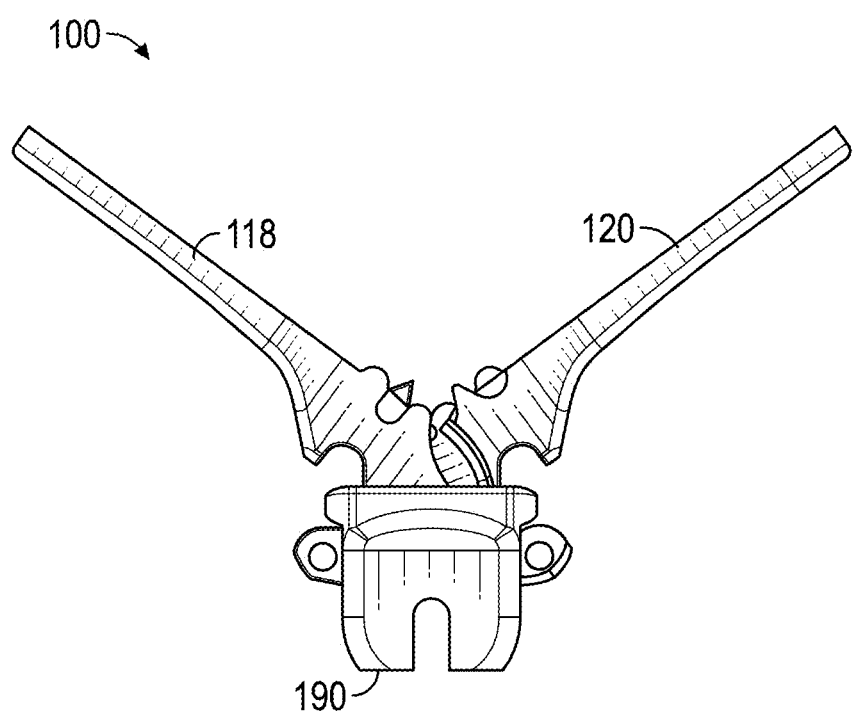
Figure 25G:
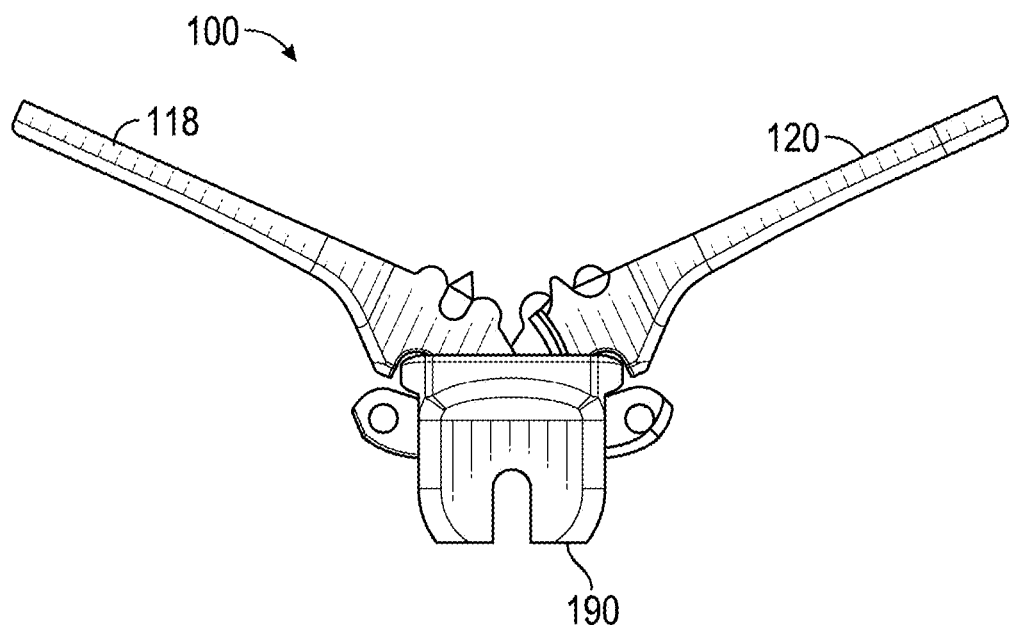
Figure 25H:
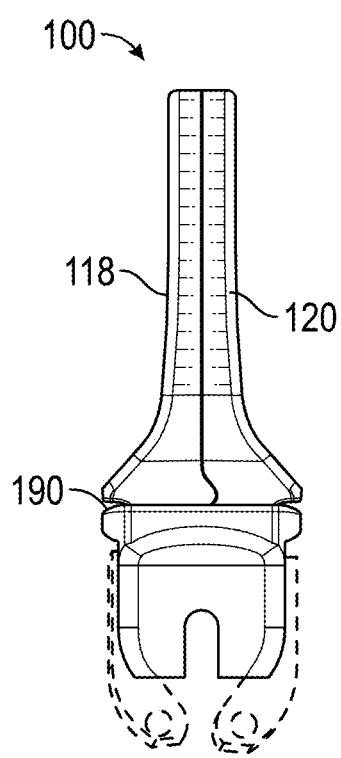

FIGS. 25E-25F illustrate an example assembly process for the instrument 100. As shown, the first and second jaw members 118, 120 can be positioned above the housing 190 (FIG. 24E). The first and second jaw members 118, 120 can be dropped into the housing 190 and rotated as shown in FIG. 25F. As shown in FIG. 25G, the first and second jaw members 118, 120 can then drop further down so that the grooves 196, 198 formed in the back of the first and second jaw members 118, 120 are concentric with the bearing surfaces 192, 194 of the housing. From this position, the first and second jaw members 118, 120 are further rotated to the position of FIG. 25H so that they are held in place by the housing 190. Although not illustrated, assembly can further include additional steps such as attaching the pulleys 122, 124 and attaching to a wrist 106, among others.

Returning to FIGS. 25A and 25B, in some embodiments, the first jaw member 118 is constrained by the second jaw member 120 and the bearing surfaces 192, 194 of the housing 190 during the entire range of motion. Once the assembly is installed in the distal clevis of the wrist 106, the range of motion can be limited to the working range of motion, which can be smaller than the angle required for disassembly.

The instrument 100 illustrated in FIGS. 25A-25B has the benefit of fewer parts and the potential to be made smaller than other embodiments. In some instances, another advantage of the present embodiment is that the slot 195 can provide more stability through tolerance issues as the slot 195 engages with either side of the pin 160 at each side of the jaws, which prevents the wrist from having torsional slop. Generally, other assembly methods require either additional parts or additional machining operations to ensure that the grips are held in their correct pivots followed by a swaging or laser welding process to join them together. This instrument 100 constrains the jaw members in the correct position in the range of motion used by the mechanism, but allows the parts to be assembled when the jaw members are over rotated. This has benefits in surgical instrument tip because as the link 126 is a single piece housing 190, it can be made smaller than other embodiments. Accordingly, in some embodiments, the link 126 can be stronger and have higher tolerances because it is a single structure. The reduced part count and reduced assembly time may reduce the cost. Some of these benefits can still be realized even if the link 126 is made out of multiple pieces.

The teeth in any of the embodiments describe above do not need to be cycloid. In some embodiments, the teeth could comprise some other profile, including involutes.

B. Determining the Mechanical Advantage/Amplification of a High Force Instrument This section discusses how one can determine the mechanical advantage of the high force instruments 100 described above. At a high level, the amplification ratio is the ratio between the input range of motion and the output range of motion. For the instruments 100 described above, the input range of motion can be related to the geometry and dimensions of the pulleys and the output range of motion can be related to the geometry and dimension of the jaw members.

When determining the mechanical advantage and amplification of these robotically controlled high force instruments 100, one metric to consider is effective pulley diameter. A high force instrument 100 can be abstracted as a mechanism that creates an output torque on a pair of jaw members from a tension applied via a pull wire or cable. The simplest way to create an output torque on the pair of jaw members is to attach the jaw members directly and rigidly to the pulley. This architecture is limited, however, in how much torque it can provide by the diameter of the pulley that can fit in the diameter of the shaft/tube through which it passes. Therefore, it is desirable to have a mechanism that can provide a mechanical advantage over a simple pulley.

Figure 26A:
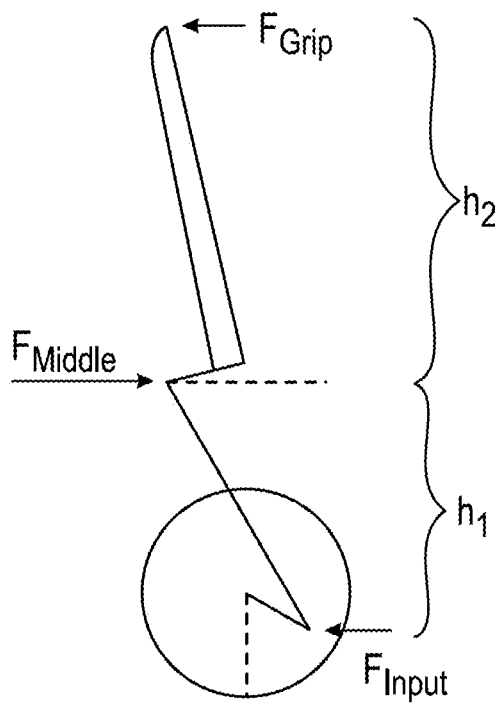
FIGS. 26A and 26B are diagrams illustrating how mechanical advantage can be determined for a high force instrument.

The mechanical advantage can be determined by calculating the pulley diameter that would have to be used to yield an equivalent gripping (output) torque. This is referred to as the effective diameter $d_{eff}$ and can be determined by Equation 1:

$$d_{eff} = \tau_{grip} * \frac{2}{F} \quad \text{(Eq. 1)}$$

wherein $d_{eff}$ is the effective diameter, $\tau_{grip}$ is the gripping (output) torque, and F is the input torque. With reference to FIG. 26A, gripping torque is related to the geometry of the jaw member by Equation 2:

$$\tau_{grip} = F_{grip} * h_2 \quad \text{(Eq. 2)}$$

Figure 26B:
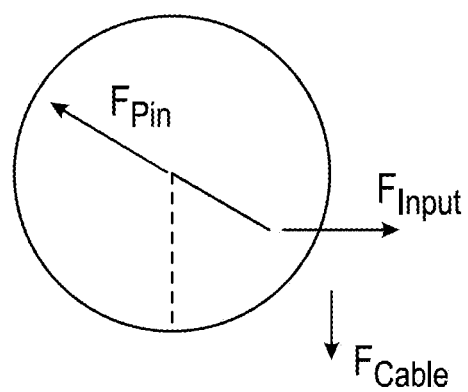

Thus, the effective diameter can be determined by Equation 3:

$$d_{eff} = F_{grip} * h_2 * \frac{2}{F_{cable}} \quad \text{(Eq. 3)}$$

wherein $F_{cable}$ is the tensile force that acts on a cable of the pulley as shown in FIG. 26B.

Figure 27:
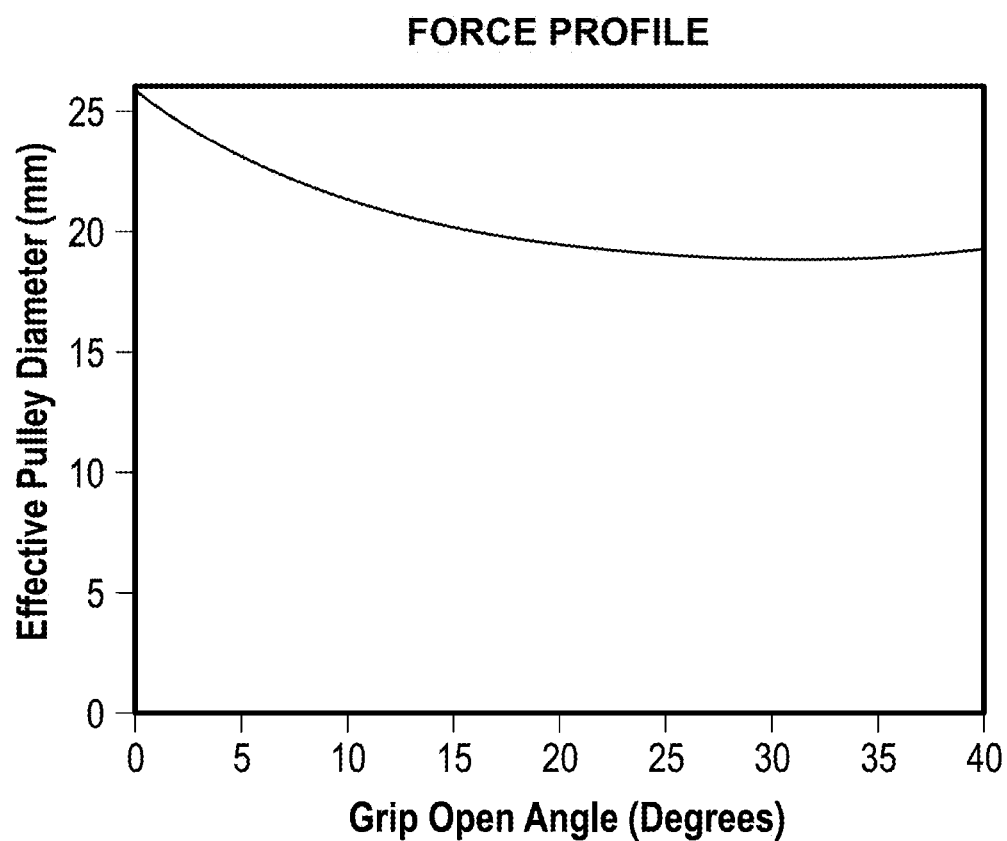
FIG. 27 is a graph depicting a force profile for one embodiment of a high force instrument.

FIG. 27 illustrates a representative force profile for one embodiment of a high force instrument 100 that is capable of having crossing drive pins (for example, similar to the embodiments of FIGS. 24A-24H and FIGS. 25A-25H). The illustrated force profile is for an instrument 100 having an 8 mm wrist and 6.7 mm drive pulleys.

The force profile shows the effective pulley diameter of the instrument 100 as a function of grip open angle. As illustrated, when the grips (jaw members) are nearly closed (0 degree open angle), the effective pulley diameter is around 26 mm. Since the diameter of the drive pulley is 6.7 mm, we are able to achieve a mechanical advantage of 3.88 times (26 mm/6.7 mm) the force that could be achieved with a simple lever and pulley system As the grip angle increases (e.g., to 40 degrees), the effective pulley diameter decreases, such that at 40 degrees, the mechanical advantage is about 3.28 times (22 mm/6.7 mm) the force that could be achieved with a simple lever and pulley system. Accordingly, we are able to achieve a mechanical advantage that is at least 3 times or greater than the force that could be achieved with a simple pulley and lever system. Furthermore, the force profile shows that our the dual drive pin design is unique in that it allows the drive pins to cross such that the grips can grip hardest at the close angle (grip open angle of zero degrees).

3. Implementing Systems and Terminology

Implementations disclosed herein provide systems, methods and apparatus for robotically-enabled medical systems. Various implementations described herein include robotically-enabled medical systems with high force instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" or "about" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system comprising:
   an instrument having an end effector, the instrument comprising:
      a first pulley configured to rotate about a pulley axis;
      a first jaw member connected to the first pulley by a first drive pin;
      a second pulley configured to rotate about the pulley axis;
      a second jaw member connected to the second pulley by a second drive pin; and
      a link providing a first pivot point about which the first jaw member can pivot and a second pivot point about which the second jaw member can pivot,
         wherein, during rotation of the first pulley and the second pulley, the first drive pin can rotate past the second drive pin.

2. The robotic system of claim 1, further comprising a robotic arm coupled to the instrument.

3. The robotic system of claim 1, wherein:
   rotation of the first pulley causes rotation of the first drive pin about the pulley axis, further causing the first jaw member to pivot about the first pivot point; and
   rotation of the second pulley causes rotation of the second drive pin about the pulley axis, further causing the second jaw member to pivot about the second pivot point.

4. The robotic system of claim 1, further comprising at least one of:
   a geared constraint configured to constrain motion of the first jaw member and the second jaw member such that motion of one of the first jaw member and the second jaw member causes a substantially corresponding motion of the other of the first jaw member and the second jaw member; and
   a slot constraint configured to prevent or reduce a risk of rotation of the end effector about the first drive pin and the second drive pin when the first drive pin and the second drive pins are aligned.

5. The robotic system of claim 1, wherein the first pulley and the second pulley can rotate to a position in which the first drive pin and second drive pin are aligned.

6. The robotic system of claim 1, wherein:
   the link comprises a housing comprising a first bearing surface spaced apart from a second bearing surface;
   the first jaw member comprises a first groove configured to pivot on the first bearing surface to form the first pivot point; and
   the second jaw member comprises a second groove configured to pivot on the second bearing surface to form the second pivot point.

7. The robotic system of claim 1, wherein the end effector is configured as a grasper, cutter, or clipper.

8. The robotic system of claim 1, wherein:
   a first link comprises a first distance between the pulley axis and a point at which an input force is applied by a cable wound on the first pulley;
   a second link comprises a second distance between the pulley axis and an axis of the first drive pin;
   a third link comprises a third distance between the axis of the first drive pin and an axis of the first pivot point;
   a fourth link comprises a fourth distance between the axis of the first pivot point and a distal end of the first jaw member.

9. The robotic system of claim 8, wherein:
   the first distance of the first link is between 3 and 4 mm;
   the second distance of the second link is between 2 and 3 mm;
   the third distance of the third link is between 7 and 8 mm; and
   the fourth distance of the fourth link is between 17 and 23 mm.

10. A robotic system comprising:
    an instrument having an end effector, the instrument comprising:
       a first pulley configured to rotate about a pulley axis;
       a first jaw member connected to the first pulley by a first drive pin;
       a second pulley configured to rotate about the pulley axis;
       a second jaw member connected to the second pulley by a second drive pin;
       a link providing a first pivot point about which the first jaw member can pivot and a second pivot point about which the second jaw member can pivot; and
       a geared constraint configured to constrain motion of the first jaw member and the second jaw member such that motion of one of the first jaw member and the second jaw member causes a substantially corresponding motion of the other of the first jaw member and the second jaw member.

11. The robotic system of claim 10, wherein the geared constraint comprises a cycloid constraint, the cycloid constraint comprising:
   a tooth formed on one of the first jaw member and the second jaw member; and
   a notch formed on the other of the first jaw member and the second jaw member.

12. The robotic system of claim 10, wherein the geared constraint comprises a pin which extends along an axis through the first jaw member and the second jaw member, wherein the pin is configured to ride within a slot formed in at least one of the first jaw member and the second jaw member.

13. The robotic system of claim 10, wherein, during rotation of the first pulley and the second pulley, the first drive pin can rotate past the second drive pin.

14. The robotic system of claim 10, wherein:
   rotation of the first pulley causes rotation of the first drive pin about the pulley axis, further causing the first jaw member to pivot about the first pivot point; and
   rotation of the second pulley causes rotation of the second drive pin about the pulley axis, further causing the second jaw member to pivot about the second pivot point.

15. The robotic system of claim 10, wherein:
   the link comprises a housing comprising a first bearing surface spaced apart from a second bearing surface;
   the first jaw member comprises a first groove configured to pivot on the first bearing surface to form the first pivot point; and
   the second jaw member comprises a second groove configured to pivot on the second bearing surface to form the second pivot point.

16. A robotic system comprising:
   an instrument having an end effector, the instrument comprising:
      a first pulley configured to rotate about a pulley axis;
      a first jaw member connected to the first pulley by a first drive pin;
      a second pulley configured to rotate about the pulley axis;
      a second jaw member connected to the second pulley by a second drive pin;
      a link providing a first pivot point about which the first jaw member can pivot and a second pivot point about which the second jaw member can pivot; and
      a slot constraint configured to prevent or reduce a risk of rotation of the end effector about the first drive pin and the second drive pin when the first drive pin and the second drive pins are aligned.

17. The robotic system of claim 16, wherein the slot constraint comprises:
   a first ear;
   a second ear spaced apart from the first ear to form a slot between the first ear and the second ear; and
   a pin extending along the pulley axis positioned within the slot.

18. The robotic system of claim 17, wherein the first ear and the second ear are each coupled to the link.

19. The robotic system of claim 16, wherein, during rotation of the first pulley and the second pulley, the first drive pin can rotate past the second drive pin.

20. The robotic system of claim 16, wherein:
   the link comprises a housing comprising a first bearing surface spaced apart from a second bearing surface;
   the first jaw member comprises a first groove configured to pivot on the first bearing surface to form the first pivot point; and
   the second jaw member comprises a second groove configured to pivot on the second bearing surface to form the second pivot point.

* * * * *

UNITED STATES PATENT AND TRADEMARK OFFICE
CERTIFICATE OF CORRECTION

PATENT NO. : 10,751,140 B2  
APPLICATION NO. : 16/429441  
DATED : August 25, 2020  
INVENTOR(S) : Daniel T. Wallace Page 1 of 1

It is certified that error appears in the above-identified patent and that said Letters Patent is hereby corrected as shown below:

In the Specification

In Column 24, Line 32, delete "Fin" and insert --$F_{in}$--.

In Column 24, Line 36, delete "Font" and insert --$F_{out}$--.

In Column 24, Line 37, delete "Font" and insert --$F_{out}$--.

In Column 24, Line 38, delete "Font" and insert --$F_{out}$--.

In Column 24, Line 38, delete "Fin." and insert --$F_{in}$.--.

In Column 24, Line 43, delete "Fin" and insert --$F_{in}$--.

In Column 24, Line 55, delete "Fin" and insert --$F_{in}$--.

In Column 24, Line 65, delete "Font" and insert --$F_{out}$--.

Signed and Sealed this  
Tenth Day of November, 2020

Andrei Iancu  
*Director of the United States Patent and Trademark Office*